(12) United States Patent
Li et al.

(10) Patent No.: US 10,273,294 B2
(45) Date of Patent: Apr. 30, 2019

(54) COMPOSITIONS AND METHODS FOR TREATING HIF-1α OVER-EXPRESSING CANCERS

(71) Applicant: University of Southern California, Los Angeles, CA (US)

(72) Inventors: Wei Li, Altadena, CA (US); David Woodley, Altadena, CA (US); Mei Chen, Altadena, CA (US); Divya Sahu, San Diego, CA (US); Hangming Dong, Guangzhou (CN); Mengchen Zou, Guangzhou (CN)

(73) Assignee: University of Southern California, Los Angeles, CA (US)

( * ) Notice: Subject to any disclaimer, the term of this patent is extended or adjusted under 35 U.S.C. 154(b) by 34 days.

(21) Appl. No.: 14/932,908

(22) Filed: Nov. 4, 2015

(65) Prior Publication Data

US 2016/0053003 A1 Feb. 25, 2016

Related U.S. Application Data

(63) Continuation-in-part of application No. 14/920,458, filed on Oct. 22, 2015, now abandoned, which is a continuation of application No. 14/225,311, filed on Mar. 25, 2014, now abandoned, which is a continuation of application No. 13/271,076, filed on Oct. 11, 2011, now abandoned.

(60) Provisional application No. 61/391,776, filed on Oct. 11, 2010, provisional application No. 62/075,129, filed on Nov. 4, 2014.

(51) Int. Cl.
*C07K 16/18* (2006.01)
*C07K 16/28* (2006.01)
*A61K 39/395* (2006.01)
*C12N 15/113* (2010.01)

(52) U.S. Cl.
CPC ........ *C07K 16/18* (2013.01); *A61K 39/39558* (2013.01); *C07K 16/2857* (2013.01); *C12N 15/113* (2013.01); *C07K 2317/34* (2013.01); *C07K 2317/76* (2013.01); *C12N 2310/10* (2013.01); *C12N 2310/14* (2013.01); *C12N 2310/20* (2017.05); *C12N 2310/531* (2013.01); *C12N 2330/50* (2013.01)

(58) Field of Classification Search
None
See application file for complete search history.

(56) References Cited

U.S. PATENT DOCUMENTS

2004/0197328 A1* 10/2004 Young ............. A61K 47/48569
424/141.1
2006/0073151 A1* 4/2006 Jay ........................ A61K 31/366
424/155.1
2007/0185017 A1 8/2007 Aggarwal et al.
2008/0207491 A1 8/2008 Ramakrishna et al.
2011/0065734 A1 3/2011 Bar et al.
2011/0280881 A1 11/2011 Udono et al.
2012/0009181 A1* 1/2012 Ab ......................... C07K 16/28
424/133.1
2012/0121595 A1 5/2012 Li et al.
2014/0199309 A1 7/2014 Li et al.

FOREIGN PATENT DOCUMENTS

| CN | 103429254 A | 12/2013 |
| CN | 107106669 A | 8/2017 |
| WO | 2009043858 A2 | 4/2009 |
| WO | 2012051207 A2 | 4/2012 |
| WO | 2016073647 A2 | 5/2016 |

OTHER PUBLICATIONS

Gura (Science, 1997, 278:1041-1042).*
Kaiser (Science, 2006, 313: 1370).*
Chames et al ( British J. of Pharmacology, 2009, 157, 220-233).*
Stellas et al. (BMC Cell Biology, Jul. 5, 2010, 11: 51, pp. 1-9).*
2014 Program (VIIIth International symposium on Heat Shock Proteins in Biology & Medicine, http://oldtown.cellstressresponses. org/preliminary-program/, retrieved May 22, 2017.*
Almagro & Fransson, Frontiers in Bioscience 2008; 13:1619-33 (Year: 2008).*
PCT/US2011/055822 International Search Report dated Oct. 12, 2012; 5 pages.
PCT/US2011/055822 Written Opinion dated Oct. 12, 2012; 6 pages.
PCT/US2011/055822 International Preliminary Report on Patentability dated Apr. 16, 2013; 7 pages.
Binder. Heat-shock protein-based vaccines for cancer and infectious disease. Expert Rev Vaccines (2008). 7 (3):383-393. Abstract Only.
GenBank Accession No. AHH00987.1. Generation and initial analysis of more than 15,000 full-length human and mouse cDNA sequences. "HSP90AA1 protein, partial [*Homo-sapiens*]" PNAS (2002).
Hwang et al. HSP90 Inhibitors: multi-targeted antitumor effects and novel combinatorial therapeutic approaches in cancer therapy. Curr Med Chem (2009). 16(24):3081-3092. Abstract Only.
Pakravan et al. Co-administration of GP96 and Her2/neu DNA vaccine in a Her2 breast cancer model. Cell Stress and Chaperones (2010). 15:977-984.
Pockley et al. The dual immunoregulatory roles of stress proteins. Trends in Biochemical Sciences (2008). 33 (2):71-79.

(Continued)

*Primary Examiner* — Peter J Reddig
(74) *Attorney, Agent, or Firm* — Nixon Peabody LLP; Linda B. Huber; Suwei Zhu

(57) ABSTRACT

Described herein are compositions that include monoclonal antibodies that specifically bind Hsp90α and methods of using the same to treat HIF-1α-overexpressing cancer. In some embodiments, the cancers are breast cancer or lung cancer. The monoclonal antibodies bind the epitope TKPI-WTRNP (SEQ ID NO: 1) in Hsp90α or VKHFSVEGQ (SEQ ID NO: 2) in Hsp90α.

12 Claims, 20 Drawing Sheets

Specification includes a Sequence Listing.

(56) References Cited

OTHER PUBLICATIONS

Quintana et al. Inhibition of adjuvant-induced arthritis by DNA vaccination with the 70-kd or the 90-kd human heat-shock protein. Arthritis & Rheumatism (2004). 58(11):3712-3720.

Quintana et al. DNA vaccines coding for heat-shock proteins (HSPs): tools for the activation of HSP-specific regulatory T cells. Expert Opinion (2005). 5(4): 1-10.

Semenza. Evaluation of HIF-1 inhibitors as anticancer agents. Drug Discovery Today (2007). 12(19):853-859.

Zhang et al. Progress on therapy targeting hypoxia-inducible factor-1. J Int. Oncol (2007). 34(7): 484-487. Abstract Only in English).

PCT/US2015/059104 International Search Report and Written Opinion dated Jul. 1, 2016; 8 pages.

Bhatia et al. Secreted heat shock protein-90 alpha (Hsp90a) is essential for skin wound healing. Annual Meeting of the Society of the Society for Investigative Dermatology, J Invest Dermatol (2015). 135:S1-S8. Abstract Only.

Jayaprakash et al. Hsp90a and Hsp90b together operate a hypoxia and nutrient paucity stress-response mechanism during wound healing. Journal of Cell Science (2015). 128:1475-1480.

Li et al. Dual Lysine Motif in Linker Region of Heat Shock Protein—90alpha defines Tumorigenicity of its Secreted Form in Breast Cancer Cells. V11th International Symposium on Heat Shock Proteins in Biology & Medicine (2014); 1 page.

Extended European Search Report of EP 15856516.8, dated Sep. 26, 2018, 9 Pages.

Divya Sahu, Characterization of a Fragment in Secreted Hsp90[alpha] with Potential Therapeutic Benefits in Wound Healing and Cancer, 2013, Dissertation Presented to the Faculty of the University of Southern California Graduate School (Genetic, Molecular and Cellular Biology), 170 Pages.

* cited by examiner

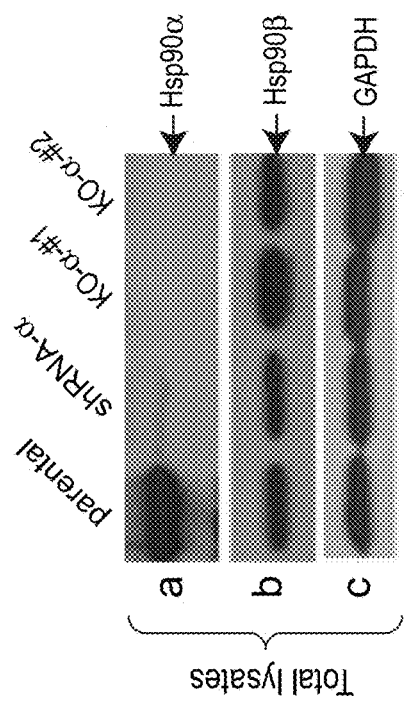
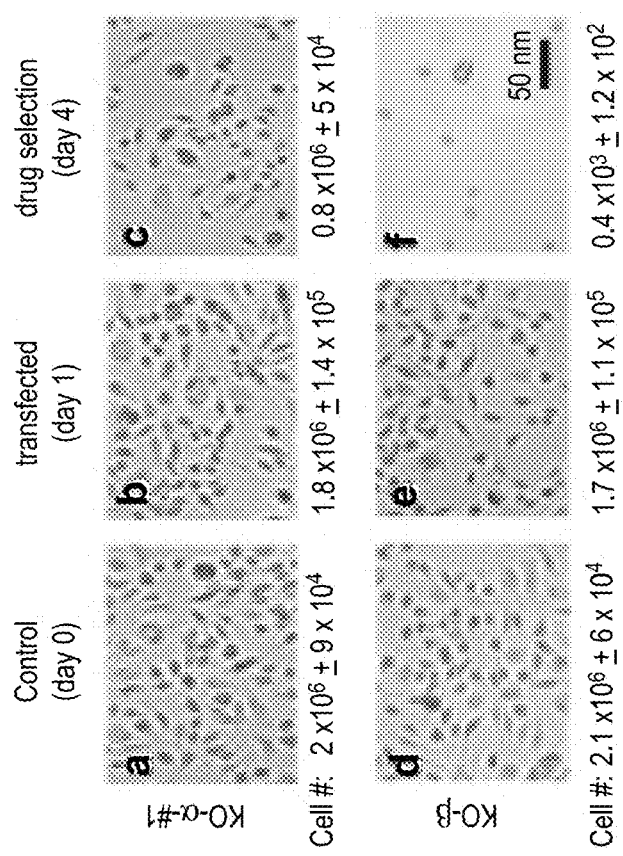
Fig. 2A
Fig. 2B

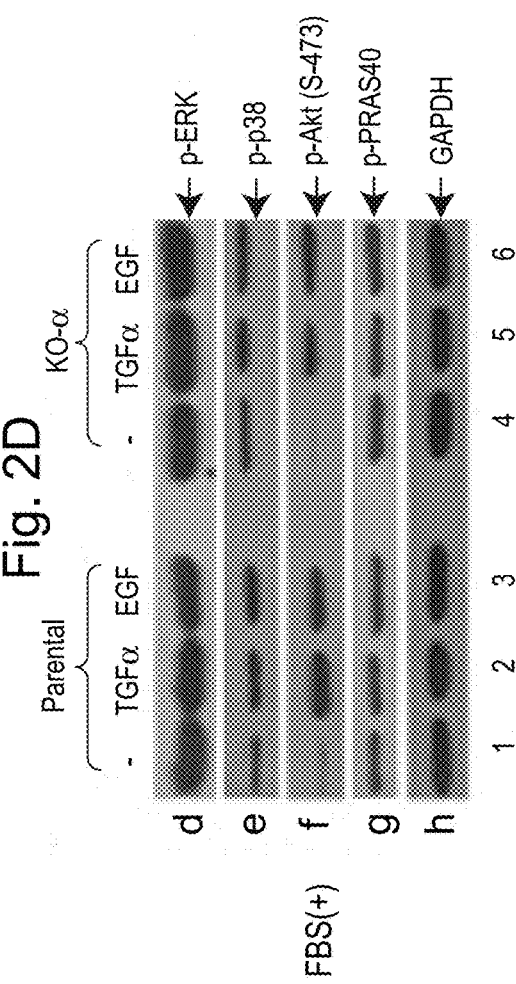
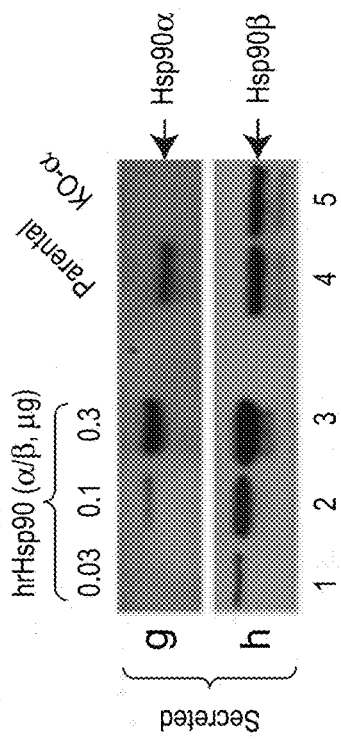
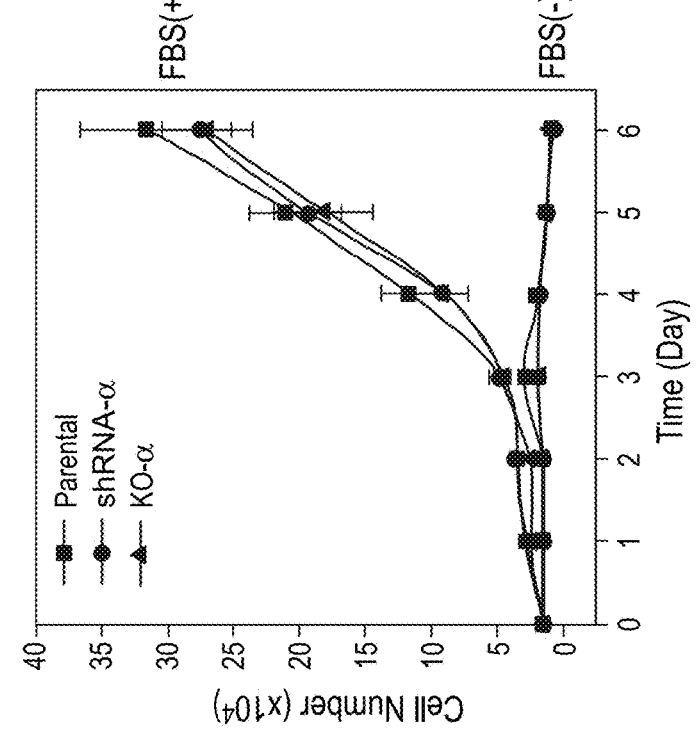

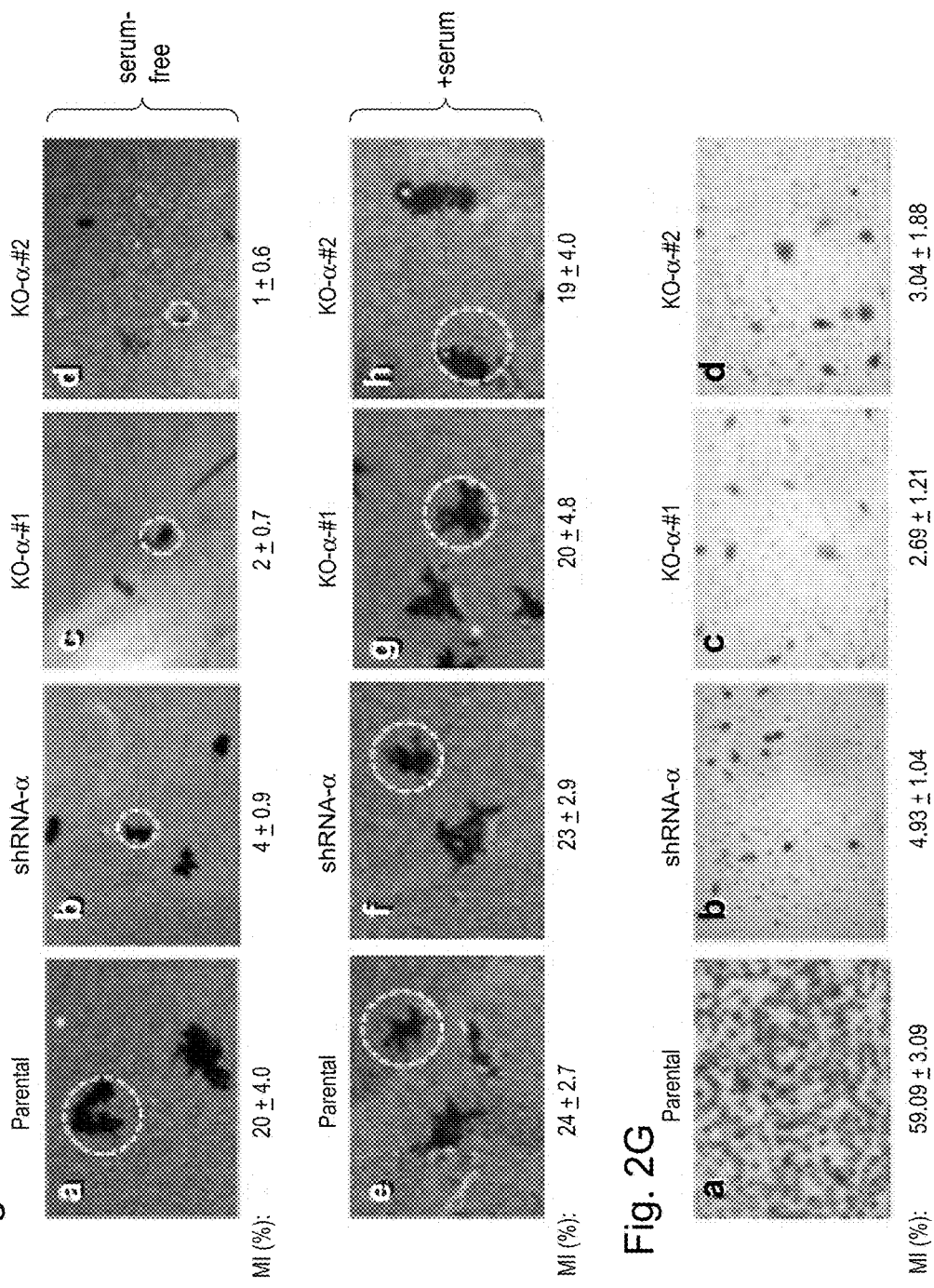

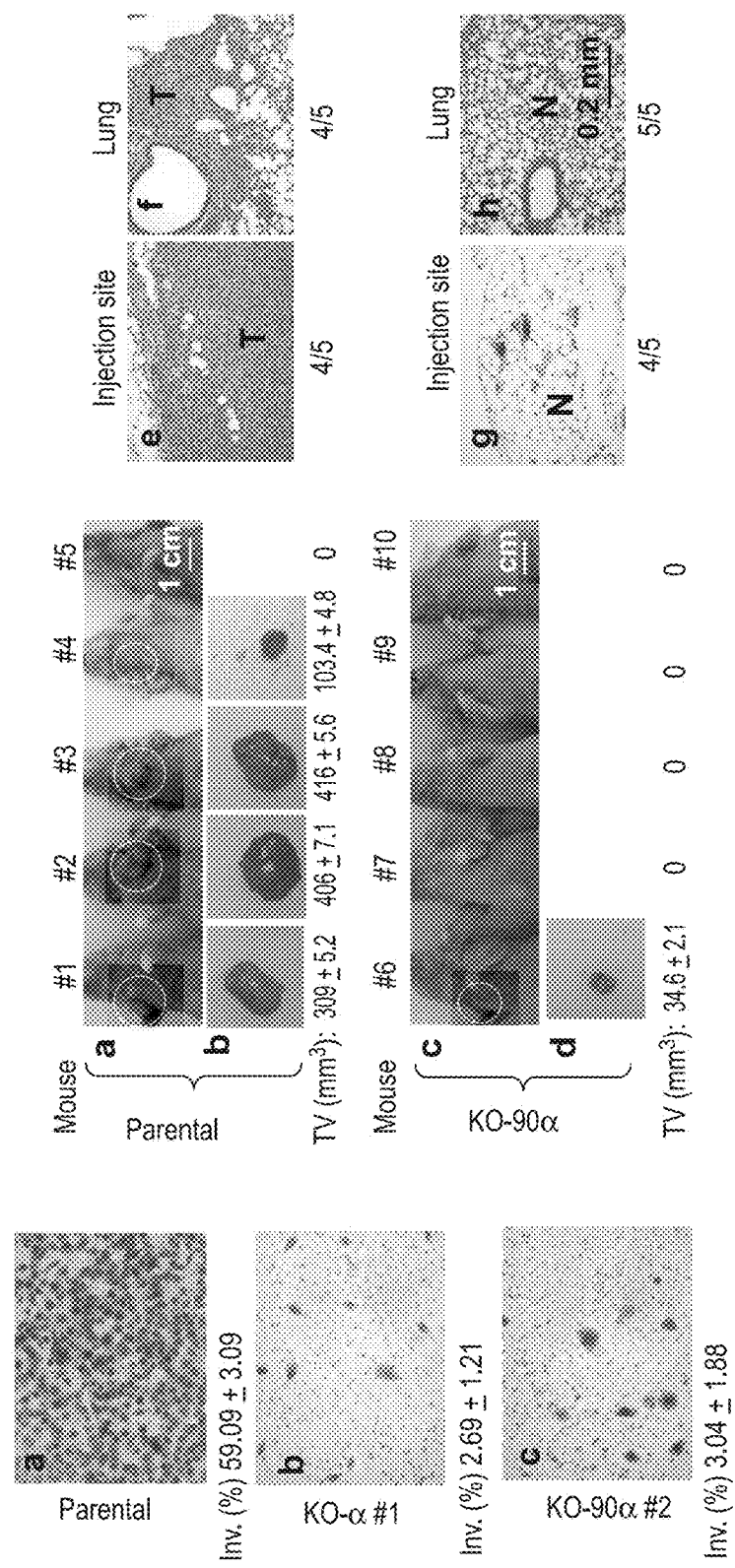

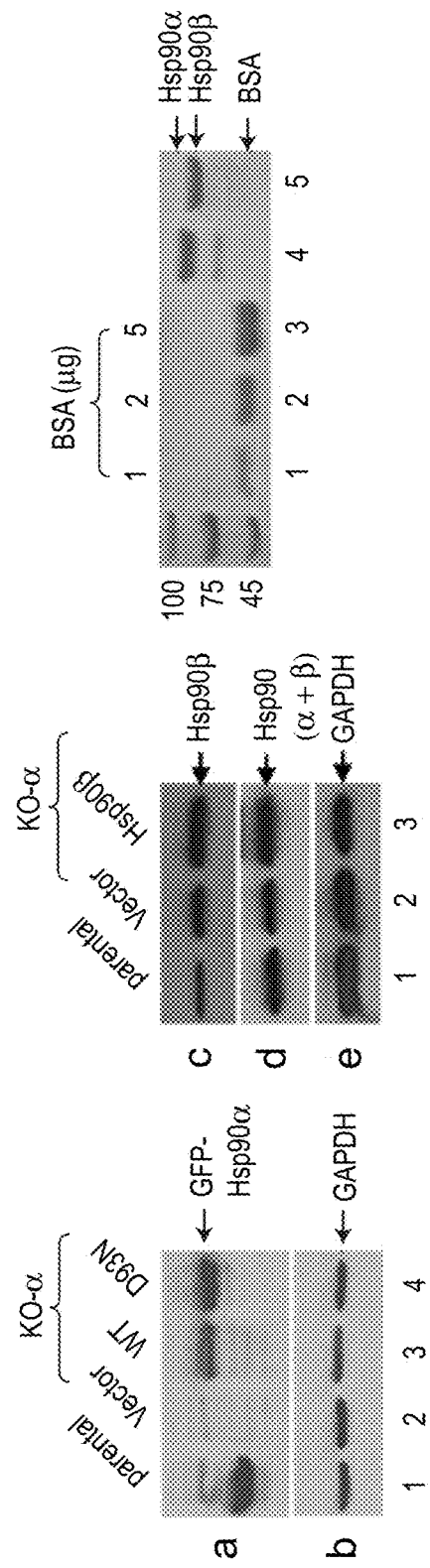

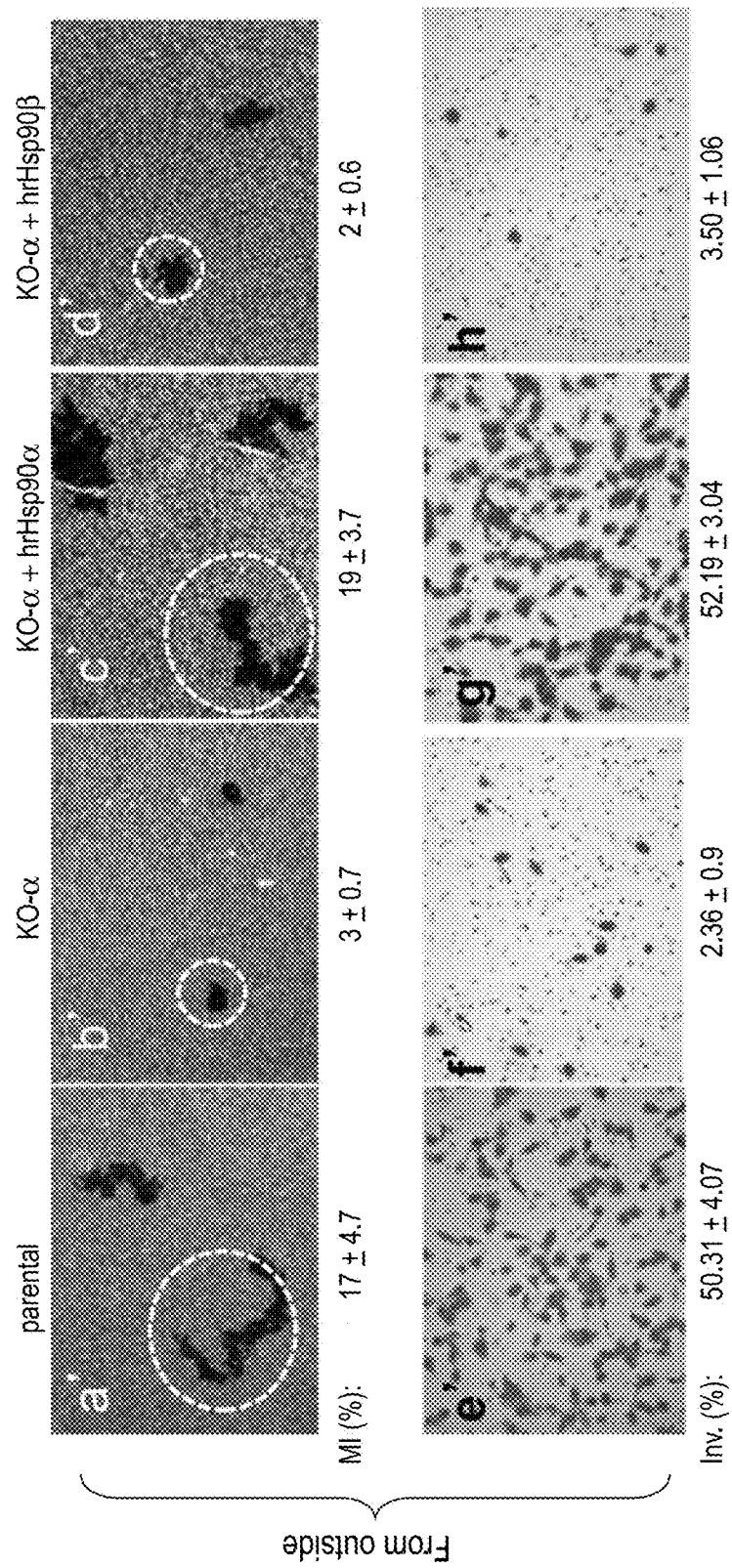

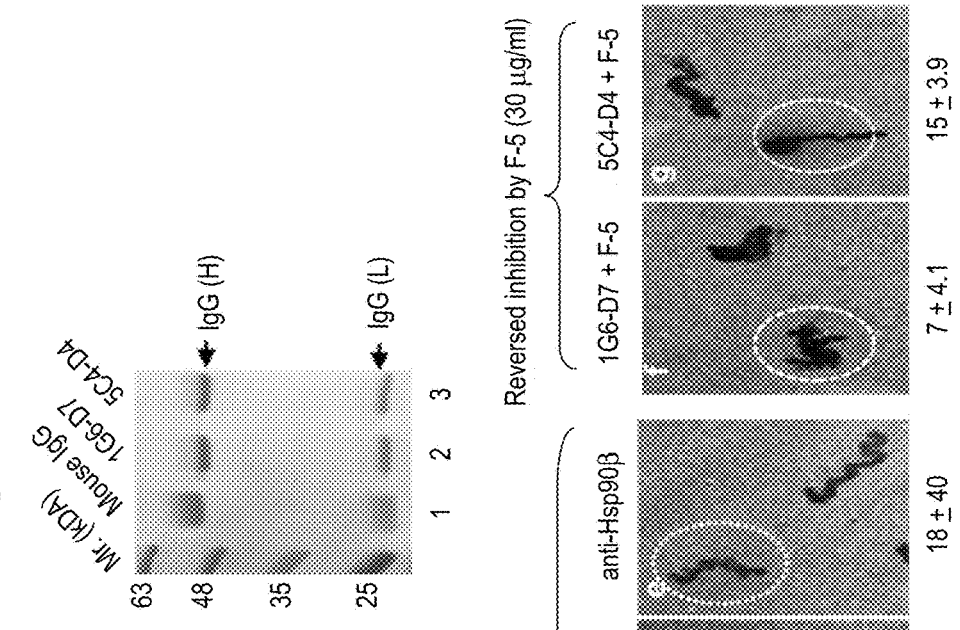
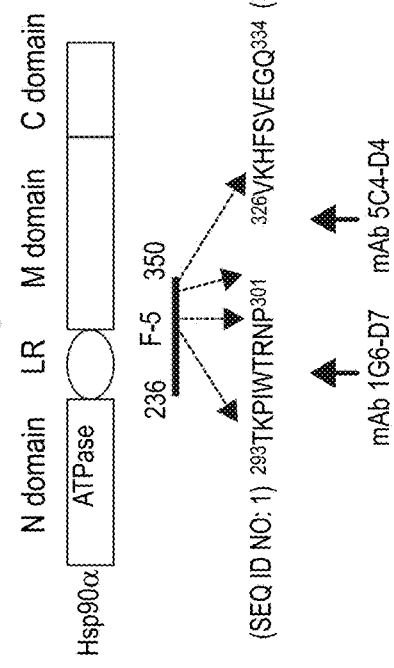
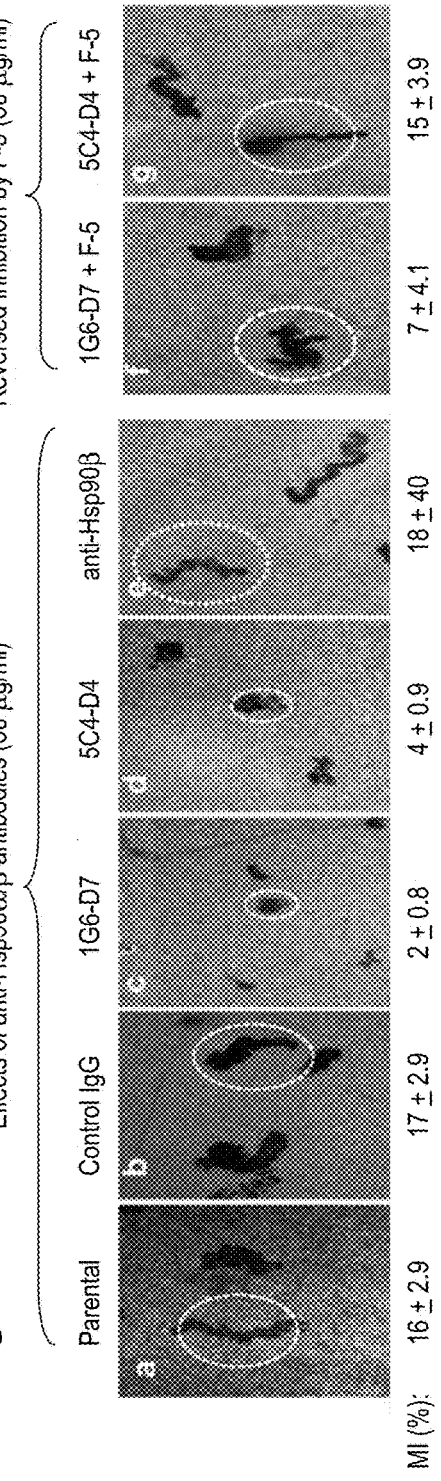

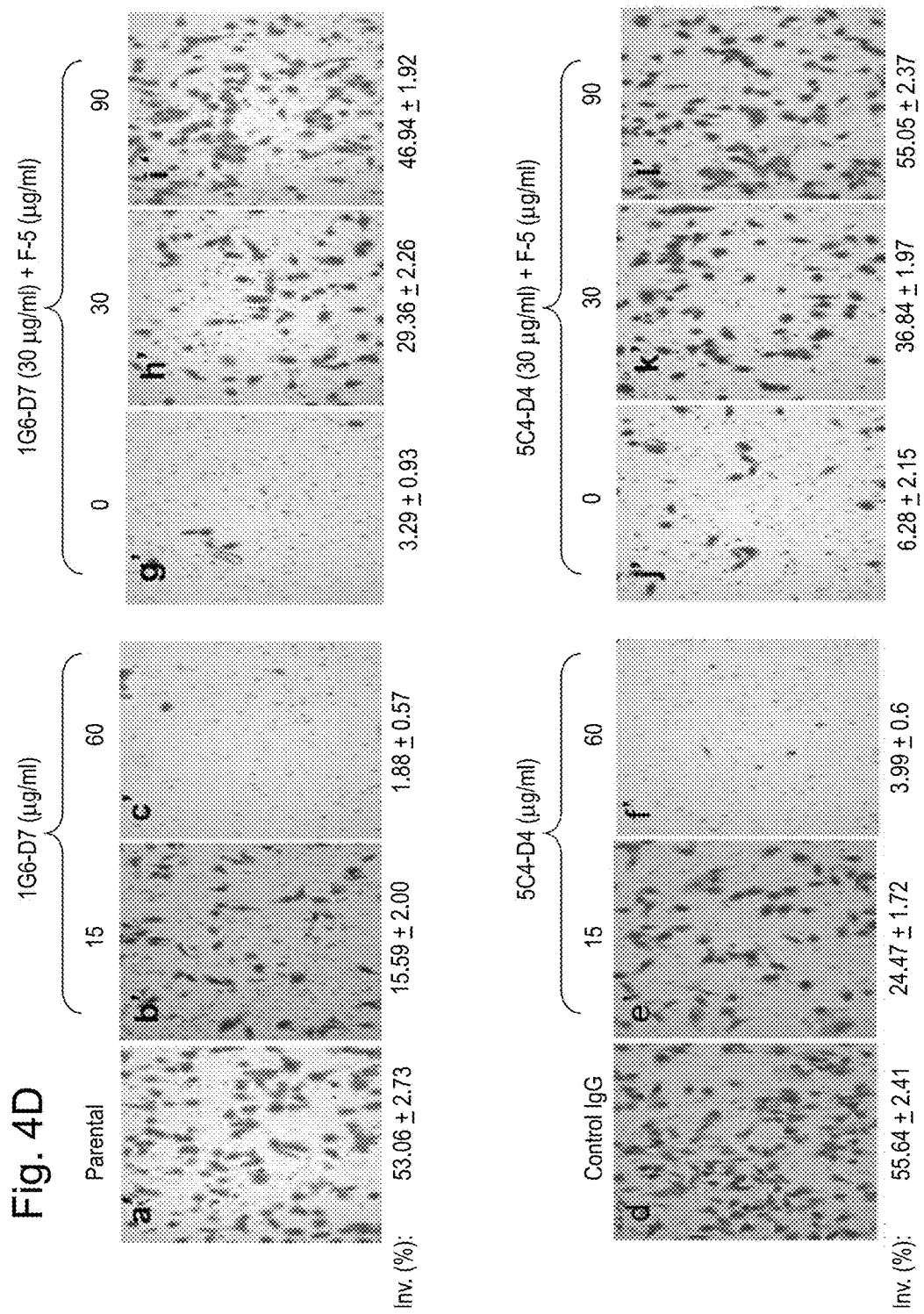

Fig. 5A

| Serum-Free Medium | | Migration Index (%) |
|---|---|---|
| Control | Non-specific peptide (BSA) | <5 ± 2.8  P<0.05 |
| Hsp90α | ATPase \| LR \| M domain \| C' domain  (1—236—272—629—732) | 22 ± 3.7  P=0.03 |
| F-5α | 236 — 350 | 25 ± 2.4  P<0.05 |
| F-6 (SEQ ID NO: 13) | 236 EEKEDKEEEKEKEEKESEDKPEIEDVGSDEEEEKKDGDKKKKKKIKEKYIDQE 289 | 18 ± 3.0  P<0.05 |
| F-7 (SEQ ID NO: 14) | 236 EEKEDKEEEKEKEEKESEDKPEIEDVG 263 | 6 ± 2.8  P<0.05 |
| F-8 (SEQ ID NO: 15) | 264 SDEEEEKKDGDKKKKKKIKEKYIDQEE 289 | 19 ± 3.9  P<0.05 |

Fig. 5B

F-8   264 SDEEEEKKDGDKKKKKKIKEKYIDQEE 289   (SEQ ID NO: 15)
F-8β  256 SDEEDDSGKDKKKKTKKIKEKYIDQEE 281   (SEQ ID NO: 16)

Fig. 5C

F-8 mutants

F-8-K277T   SDEEEEKKDGDKKKTKKIKEKYIDQEE   (SEQ ID NO: 17)
F-8-D273K   SDEEEEKKDDKKKKKKIKEKYIDQEE   (SEQ ID NO: 18)
F-8-G272D   SDEEEEKGDDDKKKKKKIKEKYIDQEE   (SEQ ID NO: 19)
F-8-D271K   SDEEEESKKGDKKKKKKIKEKYIDQEE   (SEQ ID NO: 20)
F-8-K270G   SDEEEEKGDGDKKKKKKIKEKYIDQEE   (SEQ ID NO: 21)
F-8-K269S   SDEEEESKKGDKKKKKKIKEKYIDQEE   (SEQ ID NO: 22)
F-8-E268D   SDEEEDSKKGDKKKKKKIKEKYIDQEE   (SEQ ID NO: 23)
F-8-E267D   SDEEDESKKGDKKKKKKIKEKYIDQEE   (SEQ ID NO: 24)

SEQUENCE LISTING

<160> NUMBER OF SEQ ID NOS: 24

<210> SEQ ID NO 1
<211> LENGTH: 9
<212> TYPE: PRT
<213> ORGANISM: Artificial Sequence
<220> FEATURE:
<223> OTHER INFORMATION: peptide

<400> SEQUENCE: 1

Thr Lys Pro Ile Trp Thr Arg Asn Pro
1               5

```
<210> SEQ ID NO 2
<211> LENGTH: 9
<212> TYPE: PRT
<213> ORGANISM: Artificial Sequence
<220> FEATURE:
<223> OTHER INFORMATION: peptide

<400> SEQUENCE: 2

Val Lys His Phe Ser Val Glu Gly Gln
1               5

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
ggaaagagct gcatattaa                                                  19

<210> SEQ ID NO 4
<211> LENGTH: 19
<212> TYPE: DNA
<213> ORGANISM: Artificial Sequence
<220> FEATURE:
<223> OTHER INFORMATION: Synthetic

<400> SEQUENCE: 4
gcatctatcg catgatcaa                                                  19

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
gacccaagac caaccgatgg agg                                             23

<210> SEQ ID NO 6
<211> LENGTH: 23
<212> TYPE: DNA
<213> ORGANISM: Artificial Sequence
<220> FEATURE:
<223> OTHER INFORMATION: Synthetic

<400> SEQUENCE: 6
gctgatctca taaataattt ggg                                             23

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
gacccaagac caaccgatgg                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic
```

-continued

<400> SEQUENCE: 8
gctgatctca taaataattt                                                     20

<210> SEQ ID NO 9
<211> LENGTH: 338
<212> TYPE: DNA
<213> ORGANISM: Artificial Sequence
<220> FEATURE:
<223> OTHER INFORMATION: Synthetic

<400> SEQUENCE: 9
tgtacaaaaa agcaggcttt aaaggaacca attcagtcga ctggatccgg taccaaggtc         60
gggcaggaag agggcctatt tcccatgatt ccttcatatt tgcatatacg atacaaggct        120
gttagagaga taattagaat taatttgact gtaaacacaa agatattagt acaaaatacg        180
tgacgtagaa agtaataatt tcttgggtag tttgcagttt taaaattatg ttttaaaatg        240
gactatcata tgcttaccgt aacttgaaag tatttcgatt tcttggcttt atatatcttg        300
tggaaaggac gaaacaccga cccaagacca accgatgg                                338

<210> SEQ ID NO 10
<211> LENGTH: 137
<212> TYPE: DNA
<213> ORGANISM: Artificial Sequence
<220> FEATURE:
<223> OTHER INFORMATION: Synthetic

<400> SEQUENCE: 10
gctgatctca taaataattt gttttagagc tagaaatagc aagttaaaat aaggctagtc         60
cgttatcaac ttgaaaaagt ggcaccgagt cggtgctttt tttctagacc cagctttctt        120
gtacaaagtt ggcatta                                                       137

<210> SEQ ID NO 11
<211> LENGTH: 26
<212> TYPE: DNA
<213> ORGANISM: Artificial Sequence
<220> FEATURE:
<223> OTHER INFORMATION: Synthetic

<400> SEQUENCE: 11
gcggaattct gtacaaaaaa gcaggc                                              26

<210> SEQ ID NO 12
<211> LENGTH: 27
<212> TYPE: DNA
<213> ORGANISM: Artificial Sequence
<220> FEATURE:
<223> OTHER INFORMATION: Synthetic

<400> SEQUENCE: 12
gcggaattct aatgccaact ttgtaca                                             27

<210> SEQ ID NO 13
<211> LENGTH: 53
<212> TYPE: PRT
<213> ORGANISM: Artificial Sequence
<220> FEATURE:
<223> OTHER INFORMATION: Synthetic

<400> SEQUENCE: 13

Glu Glu Lys Glu Asp Lys Glu Glu Glu Lys Glu Lys Glu Glu Lys Glu
1               5                   10                  15

```
Ser Glu Asp Lys Pro Glu Ile Glu Asp Val Gly Ser Asp Glu Glu
        20                  25                  30

Glu Lys Lys Asp Gly Asp Lys Lys Lys Lys Ile Lys Glu Lys
    35                  40                  45

Tyr Ile Asp Gln Glu
    50

<210> SEQ ID NO 14
<211> LENGTH: 27
<212> TYPE: PRT
<213> ORGANISM: Artificial Sequence
<220> FEATURE:
<223> OTHER INFORMATION: Synthetic

<400> SEQUENCE: 14

Glu Glu Lys Glu Asp Lys Glu Glu Lys Glu Lys Glu Lys Glu
1               5                   10                  15

Ser Glu Asp Lys Pro Glu Ile Glu Asp Val Gly
        20                  25

<210> SEQ ID NO 15
<211> LENGTH: 27
<212> TYPE: PRT
<213> ORGANISM: Artificial Sequence
<220> FEATURE:
<223> OTHER INFORMATION: Synthetic

<400> SEQUENCE: 15

Ser Asp Glu Glu Glu Glu Lys Lys Asp Gly Asp Lys Lys Lys Lys
1               5                   10                  15

Lys Ile Lys Glu Lys Tyr Ile Asp Gln Glu Glu
            20                  25

<210> SEQ ID NO 16
<211> LENGTH: 27
<212> TYPE: PRT
<213> ORGANISM: Artificial Sequence
<220> FEATURE:
<223> OTHER INFORMATION: Synthetic

<400> SEQUENCE: 16

Ser Asp Glu Glu Asp Asp Ser Gly Lys Asp Lys Lys Lys Thr Lys
1               5                   10                  15

Lys Ile Lys Glu Lys Tyr Ile Asp Gln Glu Glu
            20                  25

<210> SEQ ID NO 17
<211> LENGTH: 27
<212> TYPE: PRT
<213> ORGANISM: Artificial Sequence
<220> FEATURE:
<223> OTHER INFORMATION: Synthetic

<400> SEQUENCE: 17

Ser Asp Glu Glu Glu Glu Lys Lys Asp Gly Asp Lys Lys Thr Lys
1               5                   10                  15

Lys Ile Lys Glu Lys Tyr Ile Asp Gln Glu Glu
            20                  25

<210> SEQ ID NO 18
<211> LENGTH: 27
<212> TYPE: PRT
<213> ORGANISM: Artificial Sequence
```

```
<220> FEATURE:
<223> OTHER INFORMATION: Synthetic

<400> SEQUENCE: 18

Ser Asp Glu Glu Glu Lys Lys Asp Asp Lys Lys Lys Lys Lys
1               5                   10                  15

Lys Ile Lys Glu Lys Tyr Ile Asp Gln Glu Glu
            20                  25

<210> SEQ ID NO 19
<211> LENGTH: 27
<212> TYPE: PRT
<213> ORGANISM: Artificial Sequence
<220> FEATURE:
<223> OTHER INFORMATION: Synthetic

<400> SEQUENCE: 19

Ser Asp Glu Glu Glu Lys Gly Asp Asp Lys Lys Lys Lys Lys
1               5                   10                  15

Lys Ile Lys Glu Lys Tyr Ile Asp Gln Glu Glu
            20                  25

<210> SEQ ID NO 20
<211> LENGTH: 27
<212> TYPE: PRT
<213> ORGANISM: Artificial Sequence
<220> FEATURE:
<223> OTHER INFORMATION: Synthetic

<400> SEQUENCE: 20

Ser Asp Glu Glu Glu Ser Lys Lys Gly Asp Lys Lys Lys Lys
1               5                   10                  15

Lys Ile Lys Glu Lys Tyr Ile Asp Gln Glu Glu
            20                  25

<210> SEQ ID NO 21
<211> LENGTH: 27
<212> TYPE: PRT
<213> ORGANISM: Artificial Sequence
<220> FEATURE:
<223> OTHER INFORMATION: Synthetic

<400> SEQUENCE: 21

Ser Asp Glu Glu Glu Lys Gly Asp Gly Asp Lys Lys Lys Lys
1               5                   10                  15

Lys Ile Lys Glu Lys Tyr Ile Asp Gln Glu Glu
            20                  25

<210> SEQ ID NO 22
<211> LENGTH: 27
<212> TYPE: PRT
<213> ORGANISM: Artificial Sequence
<220> FEATURE:
<223> OTHER INFORMATION: Synthetic

<400> SEQUENCE: 22

Ser Asp Glu Glu Glu Glu Ser Lys Lys Gly Asp Lys Lys Lys Lys
1               5                   10                  15

Lys Ile Lys Glu Lys Tyr Ile Asp Gln Glu Glu
            20                  25

<210> SEQ ID NO 23
<211> LENGTH: 27
<212> TYPE: PRT
```

```
<213> ORGANISM: Artificial Sequence
<220> FEATURE:
<223> OTHER INFORMATION: Synthetic

<400> SEQUENCE: 23

Ser Asp Glu Glu Glu Asp Ser Lys Lys Gly Asp Lys Lys Lys Lys
1               5                   10                  15

Lys Ile Lys Glu Lys Tyr Ile Asp Gln Glu Glu
            20                  25

<210> SEQ ID NO 24
<211> LENGTH: 27
<212> TYPE: PRT
<213> ORGANISM: Artificial Sequence
<220> FEATURE:
<223> OTHER INFORMATION: Synthetic

<400> SEQUENCE: 24

Ser Asp Glu Glu Asp Glu Ser Lys Gly Asp Lys Lys Lys Lys
1               5               10                  15

Lys Ile Lys Glu Lys Tyr Ile Asp Gln Glu Glu
            20                  25
```

COMPOSITIONS AND METHODS FOR TREATING HIF-1α OVER-EXPRESSING CANCERS

CROSS-REFERENCE TO RELATED APPLICATIONS

This application is a continuation-in-part of U.S. Ser. No. 14/920,458 filed Oct. 22, 2015, now abandoned, which is a continuation of U.S. Ser. No. 14/225,311 filed Mar. 25, 2014, now abandoned, which is a continuation of U.S. Ser. No. 13/271,076 filed Oct. 11, 2011, now abandoned, which claims priority to U.S. Ser. No. 61/391,776 filed Oct. 11, 2010. This application also claims priority to U.S. Ser. No. 62/075,129 filed Nov. 4, 2014. The contents of each of the above applications are herein incorporated by reference.

STATEMENT REGARDING FEDERALLY SPONSORED RESEARCH OR DEVELOPMENT

This invention was made with government support under Grant Nos. GM066193, GM067100, AR033625 and AR046538 awarded by the National Institutes of Health. The government has certain rights in the invention.

FIELD OF INVENTION

Described herein are compositions comprising therapeutic antibodies and uses thereof to treat cancer.

BACKGROUND OF THE INVENTION

There is a need in the art for novel therapeutic agents to treat cancer. Heat shock protein-90 (Hsp90) supports tumorigenesis. Nonetheless, there is a paucity of evidence demonstrating whether intracellular or secreted form of Hsp90 plays a primary role and should be therapeutically targeted. Herein, the inventors demonstrate that the secreted, but not intracellular, Hsp90α is responsible for tumor cell's ability to migrate and invade. Knockout of Hsp90α in MDA-MB-231 cells specifically abolishes the tumor cells' intrinsic motility and invasiveness. These defects are fully rescued by addition of recombinant Hsp90α, but not Hsp90β, protein to Hsp90α-knockout cells. Monoclonal antibodies described herein, 1G6-D7 and 5C4-D, targeting the F-5 epitope of tumor cell-secreted Hsp90α block tumor cell migration and invasion. The inventors determined that Lys-270 and Lys-277 in Hsp90α determine the unique function of secreted Hsp90α and are sufficient to convert Hsp90β to a Hsp90α-like molecule to rescue motility and invasion defects in Hsp90α-knockout cells. Thus provided herein are new targets (for example, the dual lysine region of tumor-secreted Hsp90α) and new therapeutic antibodies (IG6-D7 and 5C4-D) that target Hsp90α.

SUMMARY OF THE INVENTION

Provided herein is a pharmaceutical composition comprising inhibitors of Hsp90α and a pharmaceutically acceptable carrier. In some embodiments, the inhibitors include but are not limited to any one or more of small molecule, a peptide, an antibody or a fragment thereof or a nucleic acid molecule. In various embodiments, the inhibitors target the F-5 epitope of Hsp90α. In an embodiments, the inhibitor is a nucleic acid molecule (for example, an siRNA) that targets amino acids Lys-270, Lys-277 or a combination thereof, of Hsp90α. In another embodiment, the inhibitor is a monoclonal antibody that specifically recognizes and binds Hsp90α. In an embodiment, the antibody is 1G6-D7 monoclonal antibody or a functional fragment thereof which recognizes and binds the amino acid sequence TKPIWTRNP (SEQ ID NO: 1) in Hsp90α. In another embodiment, the antibody is 5C4-D4 monoclonal antibody or a functional fragment thereof which recognizes and binds the amino acid sequence VKHFSVEGQ (SEQ ID NO: 2) in Hsp90α. In some embodiments, the 1G6-D7 and 5C4-D4 monoclonal antibodies are humanized. The functional fragments of 1G6-D7 and 5C4-D4 monoclonal antibodies retain at least one antigen binding region of the corresponding full-length antibody.

Also provided herein are methods for treating, inhibiting, preventing metastasis of, preventing relapse of and/or reducing the severity of HIF-1α-overexpressing cancer in a subject in need thereof. The methods include providing a composition comprising an inhibitor of Hsp90α and administering a therapeutically effective amount of the composition to the subject so as to treat, inhibit, prevent metastasis of, prevent relapse of and/or reduce severity of HIF-1α-overexpressing cancer in the subject. In some embodiments, the methods further comprise providing additional cancer treatments (simultaneously or sequentially with the compositions described herein). Additional cancer treatments include, but are not limited to, active surveillance, observation, surgical intervention, chemotherapy, immunotherapy, radiation therapy (such as external beam radiation, stereotactic radiosurgery (gamma knife), and fractionated stereotactic radiotherapy (FSR)), focal therapy, systemic therapy, vaccine therapies, viral therapies, molecular targeted therapies, or a combination thereof. In some embodiments, the inhibitors of Hsp90α include but are not limited to any one or more of small molecule, a peptide, an antibody or a fragment thereof or a nucleic acid molecule. In various embodiments, the inhibitor targets the F-5 epitope of Hsp90α. In an embodiments, the inhibitor is a nucleic acid molecule (for example, an siRNA) that targets Lys-270, Lys-277 or a combination thereof, of Hsp90α. In another embodiment, the inhibitor is a monoclonal antibody that specifically recognizes and binds Hsp90α. In an embodiment, the antibody is 1G6-D7 monoclonal antibody or a functional fragment thereof which binds the amino acid sequence TKPIWTRNP (SEQ ID NO: 1) in Hsp90α. In another embodiment, the antibody is 5C4-D4 monoclonal antibody or a functional fragment thereof which binds the amino acid sequence VKHFSVEGQ (SEQ ID NO: 2) in Hsp90α. In an embodiment, the inhibitors include a combination of monoclonal antibodies 1G6-D7 and 5C4-D4 or fragments thereof, administered simultaneously or sequentially. In some embodiments, the 1G6-D7 and 5C4-D4 monoclonal antibodies are humanized or human.

Also provided herein are methods for treating, inhibiting, preventing metastasis of, preventing relapse of and/or reducing the severity of breast cancer in a subject in need thereof. The methods include providing a composition comprising an inhibitor of Hsp90α and administering a therapeutically effective amount of the composition to the subject so as to treat, inhibit, prevent metastasis of, prevent relapse of and/or reduce severity of breast cancer in the subject. In some embodiments, the methods further comprise providing additional breast cancer treatments (simultaneously or sequentially with the compositions described herein). Additional cancer treatments include, but are not limited to, active surveillance, observation, surgical intervention, chemotherapy, immunotherapy, radiation therapy (such as external beam radiation, stereotactic radiosurgery (gamma knife), and fractionated stereotactic radiotherapy (FSR)), focal therapy, systemic therapy, vaccine therapies, viral therapies, molecular targeted therapies, or a combination thereof. In some embodiments, the inhibitors of Hsp90α include but are not limited to any one or more of small molecule, a peptide, an antibody or a fragment thereof or a nucleic acid molecule. In various embodiments, the inhibitor targets the F-5 epitope of Hsp90α. In an embodiments, the inhibitor is a nucleic acid molecule (for example, an siRNA) that targets Lys-270, Lys-277 or a combination thereof, of Hsp90α. In another embodiment, the inhibitor is a monoclonal antibody that specifically recognizes and binds Hsp90α. In an embodiment, the antibody is 1G6-D7 monoclonal antibody or a functional fragment thereof which binds the amino acid sequence TKPIWTRNP (SEQ ID NO: 1) in Hsp90α. In some embodiments, the 1G6-D7 monoclonal antibody is human or humanized. In another embodiment, the antibody is 5C4-D4 monoclonal antibody or a functional fragment thereof which binds the amino acid sequence VKHFSVEGQ (SEQ ID NO: 2) in Hsp90α. In some embodiments, the 5C4-D4 monoclonal antibody is human or humanized. In an embodiment, the inhibitors include a combination of monoclonal antibodies 1G6-D7 and 5C4-D4 or fragments thereof, administered simultaneously or sequentially. In some embodiments, the 1G6-D7 and 5C4-D4 monoclonal antibodies are humanized or human.

Also provided herein are methods for treating, inhibiting, preventing metastasis of, preventing relapse of and/or reducing the severity of lung cancer in a subject in need thereof. The methods include providing a composition comprising an inhibitor of Hsp90☐ and administering a therapeutically effective amount of the composition to the subject so as to treat, inhibit, prevent metastasis of, prevent relapse of and/or reduce severity of lung cancer in the subject. In some embodiments, the methods further comprise providing additional lung cancer treatments (simultaneously or sequentially with the compositions described herein). Additional cancer treatments include, but are not limited to, active surveillance, observation, surgical intervention, chemotherapy, immunotherapy, radiation therapy (such as external beam radiation, stereotactic radiosurgery (gamma knife), and fractionated stereotactic radiotherapy (FSR)), focal therapy, systemic therapy, vaccine therapies, viral therapies, molecular targeted therapies, or a combination thereof. In some embodiments, the inhibitors of Hsp90α include but are not limited to any one or more of small molecule, a peptide, an antibody or a fragment thereof or a nucleic acid molecule. In various embodiments, the inhibitor targets the F-5 epitope of Hsp90α. In an embodiments, the inhibitor is a nucleic acid molecule (for example, an siRNA) that targets Lys-270, Lys-277 or a combination thereof, of Hsp90α. In another embodiment, the inhibitor is a monoclonal antibody that specifically recognizes and binds Hsp90α. In an embodiment, the antibody is 1G6-D7 monoclonal antibody or a functional fragment thereof which binds the amino acid sequence TKPIWTRNP (SEQ ID NO: 1) in Hsp90α. In some embodiments, the 1G6-D7 monoclonal antibody is human or humanized. In another embodiment, the antibody is 5C4-D4 monoclonal antibody or a functional fragment thereof which binds the amino acid sequence VKHFSVEGQ (SEQ ID NO: 2) in Hsp90α. In some embodiments, the 5C4-D4 monoclonal antibody is human or humanized. In an embodiment, the inhibitors include a combination of monoclonal antibodies 1G6-D7 and 5C4-D4 or fragments thereof, administered simultaneously or sequentially. In some embodiments, the 1G6-D7 and 5C4-D4 monoclonal antibodies are humanized or human.

In various embodiments, the inhibitor of Hsp90α is administered intravenously, intramuscularly, intraperitonealy, orally or via inhalation. The effective amount of the inhibitor (for example, the 1G6-D7 and/or 5C4-D4 antibodies) of Hsp90α is about 1-5 mg/day, 5-10 mg/day, 10-50 mg/day, 50-100 mg/day, 100-150 mg/day, 150-200 mg/day, 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day or 2900-3000 mg/day. In some embodiments, the effective amount of the inhibitor (for example, the 1G6-D7 and/or 5C4-D4 antibodies, or fragments thereof) of Hsp90α is about 10-30 mg/kg/day.

BRIEF DESCRIPTION OF FIGURES

Exemplary embodiments are illustrated in referenced figures. It is intended that the embodiments and figures disclosed herein are to be considered illustrative rather than restrictive.

(FIG. 1B) Serum-free conditioned media (CM) were subjected to Western blot analysis for the presence of secreted Hsp90α (panel a, lanes 4, 5, 6) and Hsp90β (panel b, lanes 4, 5, 6), in comparison to known amounts of recombinant Hsp90α and Hsp90β (lanes 1, 2, 3). (FIG. 1C) The intrinsic motility of MDA-MB-231 cells are compared to migration of non-transformed HBL-100 and human keratinocytes (HK) without (upper panels) or with (lower panels) 10% fetal bovine serum using colloidal gold migration assays. Computer-assisted quantitation of the cellular migration is shown below each image as a Migration Index (MI) (Materials and methods). (FIG. 1D) The invasiveness of MDA-MB-231 cells, HBL-100 cells and HKs was compared using the Matrigel invasion assay (Methods). The quantitation is displayed below representative images (Inv. %). Data are represented as mean±SEM. p<0.05.

FIG. 2A to FIG. 2I depict, in accordance with an embodiments of the invention, Hsp90α selectively determines the motility and invasiveness of MDA-MB-231 cells, while Hsp90β is required for cell life. (FIG. 2A) Survival of MDA-MB-231 cells in drug selection following CRISPR-Cas9 Hsp90α gene (panels a, b and c) or Hsp90β gene (panels d, e and f) knockout. (FIG. 2B) Two Hsp90α-knockout clones (KO-α#1 and KO-α#2) showed complete absence of Hsp90α protein (panel a, lanes 3 and 4), in comparison to either parental control cells (lane 1) or lentivirus-mediated shRNA-Hsp90α knockdown cells (lane 2), and showed slightly elevated Hsp90β (panel b, lanes 3 and 4). (FIG. 2C) Growth curves of the parental, shRNA-Hsp90α-knockdown (shRNA-α) and Hsp90α-knockout (KO-α) MDA-MB-231 cells (±10% FBS). (FIG. 2D) Effect of Hsp90α gene knockout on indicated signaling pathways in response to EGF or TGFα. (FIG. 2E) Effects of Hsp90α gene knockout on Hsp90α and Hsp90β secretion. (FIG. 2F) Colloidal gold migration assays of the parental, Hsp90α-knockdown and Hsp90α-knockout MDA-MB-231 cells in the absence (panels a to d) or presence (panels e to h) of 10% fetal bovine serum. The Migration Index (MI) is shown beneath representative images. (FIG. 2G) Matrigel invasion assay of the same cells are shown and quantitation is displayed as the percentage (Inv. %). These results were reproducible at least in four (n≥4) independent experiments. Data are represented as mean±SEM. p<0.05. (FIG. 2H) shows matrigel invasion assay of indicated cells are shown and quantitation displayed as the percentage of invaded versus total seeded cells (Inv. %) (n≥4). (FIG. 2I) shows representative tumor formation of injected parental LM2-4175 cells (5×10$^6$) to the mammary fat pad and the tumors removed from the five mice (panels a and b). Tumor formation of injected Hsp90α-knockout LM2-4175 cells and removed tumors (panels c and d). Representative images of hematoxylin and eosin (H&E) staining of the injection site with either parental or Hsp90α-knockout LM2-4175 cells (panels e and g). Representative lung sections harvested at the end (necropsy) of the experiments (4 weeks after injection) of the indicated cell lines (panels f and h) and subjected to H&E staining T, tumor; N, normal tissue. 4/5, four out of five mice.

FIG. 3A to FIG. 3I depict, in accordance with an embodiments of the invention, secreted Hsp90α is responsible for the constitutive motility and invasiveness of the tumor cells. To rescue the motility and invasion defects of the KO-α cells, (FIG. 3A) a GFP-tagged wild type and ATPase-defective (D93N) Hsp90α cDNAs were introduced by lentiviral infection into KO-α cells and the expression was confirmed by anti-Hsp90α specific antibody (panel a, lanes 3, 4 vs. lane 1, 2). (FIG. 3B) Wild-type Hsp90β cDNA was expressed in KO-α cells as shown by Western blot analysis of the total cell lysates with anti-Hsp90β specific antibody (panel c) or anti-Hsp90 pan (α and β) antibody (panel d). (FIG. 3C) SDS-PAGE with Coomassie Brilliant Blue stain of FPLC-purified recombinant Hsp90α and Hsp90β proteins (lanes 4 and 5). (FIG. 3D) Both wt and D93N mutant Hsp90α rescued the motility defect (panels c and d vs. panel b) and invasion defect (panels h and i vs. panel g) of the KO-α cells. Little restoration occurred when Hsp90β gene was used for the rescue for either motility (panel e) or invasion (panel j). (FIG. 3E) Extracellular Hsp90α protein alone rescued all defects. (FIG. 3F) The addition of recombinant Hsp90α, (panel c' vs. b'), but not Hsp90β (panel d'), rescued the motility (panels a' to d') and invasion (panels e' to h') defects of the MDA-MB-231-KO-α cells. (FIG. 3G) The parental MDA-MB-231 tumor cells needed no rescue, because they secrete and use their own Hsp90α. (FIG. 3H) Most critically, MDA-MB-231-KO-α cells could not form tumors in mice (panel a), but addition of purified Hsp90α protein fully rescued the tumorigenicity of the cells (panels b and c). Hsp90β protein rescued much less (panel d and e) and the Hsp90α-G/T mutant did not rescue agt all (as expected, panel f). (FIG. 3I) Histochemistry (H&E) analyses showed tumor cells (panel i and k) or not (panels g and m) at the injection site (mammary fat pat) and tumor cells present (panel j) or not (panels h, l and n) in the lung (panel j). Quantitation of migration (MI, %) and invasion (Inv. %) are included. The motility assays were repeated four times, and the invasion assays were repeated three times. Data are represented as mean±SEM. p<0.05.

FIG. 4A to FIG. 4H depict, in accordance with an embodiments of the invention, mAb 1G6-D7 and mAb 5C4-D4 block tumor cell motility and invasion by targeting the F-5 region of secreted Hsp90α. (FIG. 4A) A schematic representation of two new monoclonal antibodies, 1G6-D7 and 5C4-D4, and their epitopes mapped within the F-5 region of Hsp90α. (FIG. 4B) Purified 1G6-D7 (lane 2) and 5C4-D4 (lane 3) were used in these studies. (FIG. 4C) 1G6-D7 (panel c) and 5C4-D4 (panel d), but not control IgG (panel b) or anti-Hsp90β antibody (panel e), blocked the constitutive motility of MDA-MB-231 cells (panel a). The inhibition by 1G6-D7 and 5C4-D4 was reversed by addition of excessive amount of F-5 (30 µg/ml) (panels f and g), protein. Data of the migration experiments (n=4, p<0.05) were quantitated as MI (%), as shown. (FIG. 4D) 1G6-D7 (panels a, b, c) and 5C4-D4 (panels d, e, f) antibodies blocked MDA-MB-231 cell invasion in a dose-dependent manner (panels a' to f'). The blockade was reversed by the addition of increasing amounts of F-5 (panels h', i', and panels k', l' vs. panels g' and j'). (FIG. 4E) Quantitation of the invasion is shown as the percentage of cells that invaded through the Matrigel extracellular matrix (Inv. %). (FIG. 4F) 1G6-D7 blocks tumor formation by MDA-MB-231 cells in mice, (FIG. 4G) Quantitation of data in F. (FIG. 4H) Histochemistry analysis of tumor cells at the mammary fat pad (panels a and b) and in the lung (panels c and d). The experiment was repeated four times (n=4) and results of a representative experiment shown. Data are represented as mean±SEM. p<0.05.

FIG. 5A to FIG. 5D depict, in accordance with an embodiments of the invention, Lysine-270 and lysine 277 determine the pro-motility activity of Hsp90α. (FIG. 5A) A summary of truncated Hsp90α peptides that still retain pro-motility activity of the full-length Hsp90α. The colloidal gold migration assays were carried out in serum-free medium with or without one of the listed peptides, MI (%) as shown (n=3 for each peptide, p<0.05). (FIG. 5B) Comparison of amino acid sequences between F-8 and F8β peptides, differences in eight amino acid residues marked in colors. (FIG. 5C) A schematic representation of synthetic peptides of F-8 from Hsp90α with individual substitutions of the eight amino acid residues (red) in F-8β. (FIG. 5D) Each of the mutant peptides was tested for its pro-motility activity using human keratinocytes, whose migration is inducible by recombinant Hsp90α (Note: MDA-MB-231 cells constitutively secrete Hsp90α and no longer respond to added Hsp90α). Quantitation of the migration data (n=5, p<0.05) is presented as MI (%). Data are represented as mean±SEM.

(FIG. 6A) A schematic representation of full-length Hsp90α in which lysine-270 and lysine-277 were substituted with glycine and threonine, respectively. This mutated Hsp90α is designated Hsp90α-G/T mutant. Conversely, the mutated Hsp90β in which glycine-262 and threonine-269 were substituted with lysines is designated Hsp90β-K/K mutant. Two non-specific mutations, Hsp90α-D271K and Hsp90β-K262D, were included as negative controls. (FIG. 6B) An SDS-PAGE gel stained with Coomassie Brilliant Blue of indicated amounts of bovine serum albumin (BSA, lanes 1, 2, and 3), purified wild type and mutants of Hsp90α (lanes 4, 5, 6) and wild type and mutant Hsp90β (lanes 7, 8, 9). (FIG. 6C) Rescue of the motility defect of the KO-α cells by the addition of recombinant Hsp90α and Hsp90β wild type and mutant proteins to the medium of the cells. Quantitation of the migration data (n=3, p<0.05) is presented as MI (%). (FIG. 6D) Rescue of the invasion defect of KO-α cells by the addition of wild type and mutant recombinant Hsp90α and Hsp90β proteins. Quantitation of invasion (n=4, p<0.05) was based on the percentage of the cells that penetrated through the Matrigel extracellular matrix into the lower chamber (Inv. (%). Data are represented as mean±SEM. (FIG. 6E) Dose-dependent induction of cell motility by Hsp90α-G/T and Hsp90β-K/K mutant proteins. Human dermal fibroblasts were grown to approximately 80% confluence and deprived of serum in culture medium for 16 hr. The cells were subjected to the colloidal gold migration assay in response to control (−), FBS (10%), wild type (wt) recombinant Hsp90α or indicated concentrations of Hsp90α-G/T and Hsp90β-K/K mutant proteins. Migration Index (%) is shown here (FIG. 6F) The K270G/K277G mutant acts as a dominant negative factor of MDA-MB-231 cell migration which requires secreted Hsp90α autocrine signaling. This finding suggests that the K270G/K277G mutations selectively affects the pro-motility activity, but not its binding to the LRP-1 receptor. Each experiment was repeated two times. Data are represented as mean±SEM. *p<0.0.

DETAILED DESCRIPTION

Figure 1A:
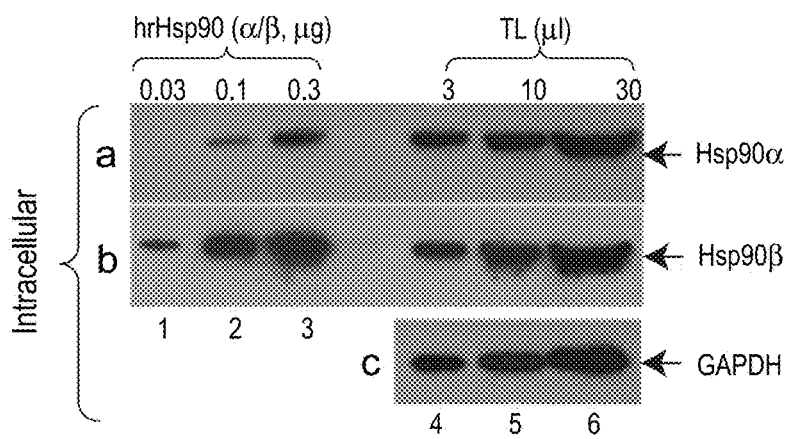
FIG. 1A to FIG. 1D depict, in accordance with an embodiments of the invention, two steady-state pools of Hsp90 proteins in MDA-MB-231 cells that show constitutive motility and invasiveness under serum-free conditions. In serum-starved MDA-MB-231 cells, (FIG. 1A) The intracellular levels of Hsp90α (panel a, lanes 4, 5, 6) and Hsp90β (panel b, lanes 4, 5, 6) are compared to known amounts of recombinant Hsp90α and Hsp90β proteins (lanes 1, 2, 3) by immunoblotting total cell lysates (TL). The slightly higher molecular mass of the recombinant proteins was due to their His tag.

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22nd ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3rd ed., revised ed., J. Wiley & Sons (New York, N.Y. 2006); Smith, March's Advanced Organic Chemistry Reactions, Mechanisms and Structure 7th ed., J. Wiley & Sons (New York, N.Y. 2013); Singleton, Dictionary of DNA and Genome Technology 3rd ed., Wiley-Blackwell (Nov. 28, 2012); and Green and Sambrook, Molecular Cloning: A Laboratory Manual 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies A Laboratory Manual 2nd ed., Cold Spring Harbor Press (Cold Spring Harbor N.Y., 2013); Köhler and Milstein, Derivation of specific antibody-producing tissue culture and tumor lines by cell fusion, Eur. J. Immunol. 1976 Jul. 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

For references on pediatrics, see Schwartz et al., The 5-Minute Pediatric Consult 4th ed., Lippincott Williams & Wilkins, (Jun. 16, 2005); Robertson et al., The Harriet Lane Handbook: A Manual for Pediatric House Officers 17th ed., Mosby (Jun. 24, 2005); and Hay et al., Current Diagnosis and Treatment in Pediatrics (Current Pediatrics Diagnosis & Treatment) 18th ed., McGraw-Hill Medical (Sep. 25, 2006).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein, the term "administering," refers to the placement an agent as disclosed herein into a subject by a method or route which results in at least partial localization of the agents at a desired site.

Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy. Beneficial or desired clinical results include, but are not limited to, alleviation of one or more symptom(s), diminishment of extent of the deficit, stabilized (i.e., not worsening) state of cancer progression, delay or slowing of metastasis or invasiveness, and amelioration or palliation of symptoms associated with the cancer. Treatment also includes a decrease in mortality or an increase in the lifespan of a subject as compared to one not receiving the treatment.

"Conditions" and "disease conditions," as used herein may include, but are in no way limited to any form of cancer. In an embodiment, the cancer is a HIF-1α-overexpressing cancer.

"Subject" or "individual" or "animal" or "patient" or "mammal," is meant any subject, particularly a mammalian subject, for whom diagnosis, prognosis, or therapy is desired. In some embodiments, the subject has cancer. In some embodiments, the subject had cancer at some point in the subject's lifetime. In various embodiments, the subject's cancer is in remission, is recurrent or is non-recurrent. The subject may be human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets. The term does not denote a particular age or sex. Thus, adult and newborn subjects, as well as fetuses, whether male or female, are intended to be included within the scope of this term.

"Mammal" as used herein refers to any member of the class Mammalia, including, without limitation, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject. The term does not denote a particular age or sex. Thus, adult and newborn subjects, as well as fetuses, whether male or female, are intended to be included within the scope of this term.

"Therapeutic agents" as used herein refers to agents that are used to, for example, treat, inhibit, prevent, mitigate the effects of, reduce the severity of, reduce the likelihood of developing, slow the progression of and/or cure, a disease. Diseases targeted by the therapeutic agents include but are not limited to cancer.

The term "effective amount" as used herein refers to the amount of a pharmaceutical composition comprising one or more peptides as disclosed herein or a mutant, variant, analog or derivative thereof, to decrease at least one or more symptom of the disease or disorder, and relates to a sufficient amount of pharmacological composition to provide the desired effect. The phrase "therapeutically effective amount" as used herein means a sufficient amount of the composition to treat a disorder, at a reasonable benefit/risk ratio applicable to any medical treatment.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject or the state of the subject prior to administering the peptide. Measured or measurable parameters include clinically detectable markers of disease, for example, elevated or depressed levels of a biological marker, as well as parameters related to a clinically accepted scale of symptoms or markers for fibrosis and/or inflammation. It will be understood, however, that the total daily usage of the compositions and formulations as disclosed herein will be decided by the attending physician within the scope of sound medical judgment. The exact amount required will vary depending on factors such as the type of disease being treated, gender, age, and weight of the subject.

"Chemotherapeutic drugs" or "chemotherapeutic agents" as used herein refer to drugs used to treat cancer including but not limited to Albumin-bound paclitaxel (nab-paclitaxel), Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, Epirubicin, Epothilone, Erlotinib, Etoposide, Fluorouracil, Gefitinib, Gemcitabine, Hydroxyurea, Idarubicin, Imatinib, Ipilimumab, Irinotecan, Mechlorethamine, Melphalan, Mercaptopurine, Methotrexate, Mitoxantrone, Ocrelizumab, Ofatumumab, Oxaliplatin, Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, or a combination thereof.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder, such as cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

"A "cancer" or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign and malignant cancers, as well as dormant tumors or micrometastatses. Cancers which migrate from their original location and seed vital organs can eventually lead to the death of the subject through the functional deterioration of the affected organs. As used herein, the term "carcinoma" refers to a cancer arising from epithelial cells. As used herein, the term "invasive" refers to the ability to infiltrate and destroy surrounding tissue. Melanoma is an invasive form of skin tumor. Examples of cancer include, but are not limited to B-cell lymphomas (Hodgkin's lymphomas and/or non-Hodgkins lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer.

"HIF-1" as used herein refers to hypoxia-inducible factor-1. HIF-1α-overexpressing cancer refers to cancers in which HIF-1α is overexpressed in tumor cells. The majority of common human cancers in at least 15 organs overexpress HIF-1α (see the complete list by G. L. Semenza (2007) Drug Discovery Today, Vol. 12, Page 853-859).

"LRP-1" or "LRP1" as used herein refers to low density lipoprotein receptor-related protein 1, also known as alpha-2-macroglobulin receptor (A2MR), apolipoprotein E receptor (APOER) or cluster of differentiation 91 (CD91). LRP-1 is a receptor for Hsp90α.

"HSP90α" or "Hsp90α" as used herein refers to the heat shock protein 90α.

"Isolated Hsp90α", "purified Hsp90α", "isolated fragments of Hsp90α" or "purified fragments of Hsp90α" as used herein refer to Hsp90α proteins or fragments thereof that are expressed and removed from non-Hsp90α or fragments thereof and/or removed from cellular constituent that are associated with or impair the activity of Hsp90α or fragments there.

"Antibody" as used herein refers to polyclonal antibodies, monoclonal antibodies, humanized antibodies, single-chain antibodies, and fragments thereof such as Fab, F(ab')$_2$, Fv, and other fragments which retain the antigen binding function of the parent antibody. In an embodiment, the antibody specifically binds Hsp90α as described herein. The antibody may be polyclonal antibodies, monoclonal antibodies, humanized antibodies, single-chain antibodies, and fragments thereof such as Fab, F(ab')2, Fv, and other fragments which retain the sialidase activity of the parent antibody. The antibody may be a recombinant antibody. The term "recombinant human antibody" can include a human antibody produced using recombinant DNA technology.

"Monoclonal antibody" as used herein refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')2, Fv, and others which retain the antigen binding function of the antibody. Monoclonal antibodies of any mammalian species can be used in this invention. In practice, however, the antibodies will typically be of rabbit or murine origin because of the availability of rabbit or murine cell lines for use in making the required hybrid cell lines or hybridomas to produce monoclonal antibodies. "Human monoclonal antibody" can include a monoclonal antibody with substantially or entirely human CDR amino acid sequences produced, for example by recombinant methods such as production by a phage library, by lymphocytes or by hybridoma cells "Humanized antibodies" as used herein means that at least a portion of the framework regions of an immunoglobulin are derived from human immunoglobulin sequences. The term "humanised antibody" can mean an antibody from a non-human species (e.g. mouse) whose protein sequences have been modified to increase their similarity to antibodies produced naturally in humans.

"Single chain antibodies" as used herein refer to antibodies prepared by determining the binding domains (both heavy and light chains) of a binding antibody, and supplying a linking moiety which permits preservation of the binding function. This forms, in essence, a radically abbreviated antibody, having only that part of the variable domain necessary for binding to the antigen. Determination and construction of single chain antibodies are described in U.S. Pat. No. 4,946,778 to Ladner et al.

The term "antigen binding region" can mean a region of the antibody having specific binding affinity for its target antigen, for example, the HSP90α protein, or an epitope thereof. The binding region may be a hypervariable CDR or a functional portion thereof. The term "functional portion" of a CDR can mean a sequence within the CDR which shows specific affinity for the target antigen. The functional portion of a CDR may comprise a ligand which specifically binds to Hsp90α protein.

The term "CDR" can mean a hypervariable region in the heavy and light variable chains. There may be one, two, three or more CDRs in each of the heavy and light chains of the antibody. Normally, there are at least three CDRs on each chain which, when configured together, form the antigen-binding site, i.e. the three-dimensional combining site with which the antigen binds or specifically reacts. It has however been postulated that there may be four CDRs in the heavy chains of some antibodies.

The definition of CDR also includes overlapping or subsets of amino acid residues when compared against each other. The exact residue numbers which encompass a particular CDR or a functional portion thereof will vary depending on the sequence and size of the CDR. Those skilled in the art can routinely determine which residues comprise a particular CDR given the variable region amino acid sequence of the antibody.

The term "functional fragment" of an antibody can mean a portion of the antibody which retains a functional activity. A functional activity can be, for example antigen binding activity or specificity. A functional activity can also be, for example, an effector function provided by an antibody constant region. The term "functional fragment" is also intended to include, for example, fragments produced by protease digestion or reduction of a human monoclonal antibody and by recombinant DNA methods known to those skilled in the art. Human monoclonal antibody functional fragments include, for example individual heavy or light chains and fragments thereof, such as VL, VH and Fd; monovalent fragments, such as Fv, Fab, and Fab; bivalent fragments such as F(ab')2; single chain Fv (scFv); and Fc fragments.

The term "VL fragment" can mean a fragment of the light chain of a human monoclonal antibody which includes all or part of the light chain variable region, including the CDRs. A VL fragment can further include light chain constant region sequences.

The term "VH fragment" can means a fragment of the heavy chain of a human monoclonal antibody which includes all or part of the heavy chain variable region, including the CDRs.

The term "Fd fragment" can mean the light chain variable and constant regions coupled to the heavy chain variable and constant regions, i.e. VL, CL and VH, CH-1.

The term "Fv fragment" can mean a monovalent antigen-binding fragment of a human monoclonal antibody, including all or part of the variable regions of the heavy and light chains, and absent of the constant regions of the heavy and light chains. The variable regions of the heavy and light chains include, for example, the CDRs. For example, an Fv fragment includes all or part of the amino terminal variable region of about 110 amino acids of both the heavy and light chains.

The term "Fab fragment" can mean a monovalent antigen-binding fragment of a human monoclonal antibody that is larger than an Fv fragment. For example, a Fab fragment includes the variable regions, and all or part of the first constant domain of the heavy and light chains. Thus, a Fab fragment additionally includes, for example, amino acid residues from about 110 to about 220 of the heavy and light chains.

The term "Fab' fragment" can mean a monovalent antigen-binding fragment of a human monoclonal antibody that is larger than a Fab fragment. For example, a Fab' fragment includes all of the light chain, all of the variable region of the heavy chain, and all or part of the first and second constant domains of the heavy chain. For example, a Fab' fragment can additionally include some or all of amino acid residues 220 to 330 of the heavy chain.

The term "F(ab')2 fragment" can mean a bivalent antigen-binding fragment of a human monoclonal antibody. An F(ab')2 fragment includes, for example, all or part of the variable regions of two heavy chains- and two light chains, and can further include all or part of the first constant domains of two heavy chains and two light chains.

The term "single chain Fv (scFv)" can mean a fusion of the variable regions of the heavy (VH) and light chains (VL) connected with a short linker peptide.

The term "bispecific antibody (BsAb)" can mean a bispecific antibody comprising two scFv linked to each other by a shorter linked peptide.

Heat shock protein-90 (Hsp90) is known as an ATPase-driven intracellular chaperone and hopeful target for anti-tumor therapeutics, although small molecule inhibitors targeting the ATPase of Hsp90 proteins in patient clinical trials have not been successful. Nonetheless, there is a paucity of evidence demonstrating whether it is the intracellular or the secreted form of Hsp90 that plays a primary role and, therefore, should be therapeutically targeted. The inventors find that: 1) it is the secreted form of Hsp90α (not intracellular Hsp90α and not intracellular or extracellular Hsp90β) that is responsible for tumor cell motility and invasion; 2) Lys-270 and Lys-277 in Hsp90α determine the unique function of secreted Hsp90α and substitutions with the two lysines are sufficient to convert Hsp90β to a Hsp90α-like molecule; 3) newly developed monoclonal antibodies, 1G6-D7 and 5C4-D, targeting the key epitope, F-5, in tumor-secreted Hsp90α shows a strong therapeutic potential. This study suggests that selectively targeting tumor-secreted Hsp90α is a safer and more effective anti-cancer approach.

Provided herein are methods for treating HIF-1α-overexpressing cancer in a subject in need thereof. The methods include providing a composition comprising an inhibitor of Hsp90α and administering a therapeutically effective amount of the composition to the subject so as to treat HIF-1α-overexpressing cancer in the subject. In some embodiments, the inhibitors of Hsp90α include but are not limited to any one or more of small molecule, a peptide, an antibody or a fragment thereof or a nucleic acid molecule. In various embodiments, the inhibitor targets the F-5 epitope of Hsp90α. In an embodiments, the inhibitor is a nucleic acid molecule (for example, an siRNA) that targets Lys-270, Lys-277 or a combination thereof, of Hsp90α. In another embodiment, the inhibitor is a monoclonal antibody that specifically recognizes and binds Hsp90α. In an embodiment, the antibody is 1G6-D7 monoclonal antibody or a functional fragment thereof which binds the amino acid sequence TKPIWTRNP (SEQ ID NO: 1) in Hsp90α. In another embodiment, the antibody is 5C4-D4 monoclonal antibody or a functional fragment thereof which binds the amino acid sequence VKHFSVEGQ (SEQ ID NO: 2) in Hsp90α. In one embodiment, the cancer is breast cancer. In another embodiment, the cancer is lung cancer.

Also provided herein are methods for inhibiting HIF-1α-overexpressing cancer in a subject in need thereof. The methods include providing a composition comprising an inhibitor of Hsp90α and administering a therapeutically effective amount of the composition to the subject so as to inhibit HIF-1α-overexpressing cancer in the subject. In some embodiments, the inhibitors of Hsp90α include but are not limited to any one or more of small molecule, a peptide, an antibody or a fragment thereof or a nucleic acid molecule. In various embodiments, the inhibitor targets the F-5 epitope of Hsp90α. In an embodiments, the inhibitor is a nucleic acid molecule (for example, an siRNA) that targets Lys-270, Lys-277 or a combination thereof, of Hsp90α. In another embodiment, the inhibitor is a monoclonal antibody that specifically recognizes and binds Hsp90α. In an embodiment, the antibody is 1G6-D7 monoclonal antibody or a functional fragment thereof which binds the amino acid sequence TKPIWTRNP (SEQ ID NO: 1) in Hsp90α. In another embodiment, the antibody is 5C4-D4 monoclonal antibody or a functional fragment thereof which binds the amino acid sequence VKHFSVEGQ (SEQ ID NO: 2) in Hsp90α. In one embodiment, the cancer is breast cancer. In another embodiment, the cancer is lung cancer.

Further provided herein are methods for preventing metastasis of HIF-1α-overexpressing cancer in a subject in need thereof. The methods include providing a composition comprising an inhibitor of Hsp90α and administering a therapeutically effective amount of the composition to the subject so as to prevent metastasis of HIF-1α-overexpressing cancer in the subject. In some embodiments, the inhibitors of Hsp90α include but are not limited to any one or more of small molecule, a peptide, an antibody or a fragment thereof or a nucleic acid molecule. In various embodiments, the inhibitor targets the F-5 epitope of Hsp90α. In an embodiments, the inhibitor is a nucleic acid molecule (for example, an siRNA) that targets Lys-270, Lys-277 or a combination thereof, of Hsp90α. In another embodiment, the inhibitor is a monoclonal antibody that specifically recognizes and binds Hsp90α. In an embodiment, the antibody is 1G6-D7 monoclonal antibody or a functional fragment thereof which binds the amino acid sequence TKPIWTRNP (SEQ ID NO: 1) in Hsp90α. In another embodiment, the antibody is 5C4-D4 monoclonal antibody or a functional fragment thereof which binds the amino acid sequence VKHFSVEGQ (SEQ ID NO: 2) in Hsp90α. In one embodiment, the cancer is breast cancer. In another embodiment, the cancer is lung cancer.

Also provided herein are methods for reducing the severity of HIF-1α-overexpressing cancer in a subject in need thereof. The methods include providing a composition comprising an inhibitor of Hsp90α and administering a therapeutically effective amount of the composition to the subject so as to reduce the severity of HIF-1α-overexpressing cancer in the subject. In some embodiments, the inhibitors of Hsp90α include but are not limited to any one or more of small molecule, a peptide, an antibody or a fragment thereof or a nucleic acid molecule. In various embodiments, the inhibitor targets the F-5 epitope of Hsp90α. In an embodiments, the inhibitor is a nucleic acid molecule (for example, an siRNA) that targets Lys-270, Lys-277 or a combination thereof, of Hsp90α. In another embodiment, the inhibitor is a monoclonal antibody that specifically recognizes and binds Hsp90α. In an embodiment, the antibody is 1G6-D7 monoclonal antibody which binds the amino acid sequence TKPIWTRNP (SEQ ID NO: 1) in Hsp90α. In another embodiment, the antibody is 5C4-D4 monoclonal antibody which binds the amino acid sequence VKHFSVEGQ (SEQ ID NO: 2) in Hsp90α. In one embodiment, the cancer is breast cancer. In another embodiment, the cancer is lung cancer.

In various embodiments, the methods described herein further comprise providing additional cancer treatments (simultaneously or sequentially). Additional cancer treatments include, but are not limited to, active surveillance, observation, surgical intervention, chemotherapy, immunotherapy, radiation therapy (such as external beam radiation, stereotactic radiosurgery (gamma knife), and fractionated stereotactic radiotherapy (FSR)), focal therapy, systemic therapy, vaccine therapies, viral therapies, molecular targeted therapies, or a combination thereof. In some embodiments, the antibodies described herein are conjugated to therapeutic agents to form, for example, antibody-protein toxin conjugates (Immunotoxins), antibody-radionuclide conjugates, antibody-drug conjugates (Teicher and Chari, *Clin Cancer Res* Oct. 15, 2011 Vol 17; 6389-6397).

In some embodiments, chemotherapeutic agents may be selected from any one or more of cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: treosulfan, and trofosfamide; plant alkaloids: vinblastine, paclitaxel, docetaxol; DNA topoisomerase inhibitors: doxorubicin, epirubicin, etoposide, camptothecin, topotecan, irinotecan, teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2)

inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.).

In various embodiments, additional therapies include, for example, radiation therapy. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or tele-therapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In various embodiments, additional therapies include, for example, immunotherapy. Immunotherapy may comprise, for example, use of cancer vaccines and/or sensitized antigen presenting cells. In some embodiments, therapies include targeting cells in the tumor microenvironment or targeting immune cells. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines.

In various embodiments, additional therapies include, for example, hormonal therapy, Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In various embodiments, the effective amount of the inhibitor of Hsp90α (for example, monoclonal antibodies 1G6-D7, 5C4-D4 or a combination thereof) is any one or more of about 0.01 to 0.05 µg/kg/day, 0.05-0.1 µg/kg/day, 0.1 to 0.5 µg/kg/day, 0.5 to 5 µg/kg/day, 5 to 10 µg/kg/day, 10 to 20 µg/kg/day, 20 to 50 µg/kg/day, 50 to 100 µg/kg/day, 100 to 150 µg/kg/day, 150 to 200 µg/kg/day, 200 to 250 µg/kg/day, 250 to 300 µg/kg/day, 300 to 350 µg/kg/day, 350 to 400 µg/kg/day, 400 to 500 µg/kg/day, 500 to 600 µg/kg/day, 600 to 700 µg/kg/day, 700 to 800 µg/kg/day, 800 to 900 µg/kg/day, 900 to 1000 µg/kg/day, 0.01 to 0.05 mg/kg/day, 0.05-0.1 mg/kg/day, 0.1 to 0.5 mg/kg/day, 0.5 to 1 mg/kg/day, 1 to 5 mg/kg/day, 5 to 10 mg/kg/day, 10 to 15 mg/kg/day, 15 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day, 900 to 1000 mg/kg/day or a combination thereof. In some embodiments, the effective amount of the inhibitor (for example, the 1G6-D7 and/or 5C4-D4 antibodies, or fragments thereof) of Hsp90α is about 10-30 mg/kg/day. Typical dosages of an effective amount of the Hsp90α inhibitor can be in the ranges recommended by the manufacturer where known therapeutic compounds are used, and also as indicated to the skilled artisan by the in vitro responses or responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, such as biopsied malignant tumors, or the responses observed in the appropriate animal models. In various embodiments, the compositions of the invention comprising the Hsp90α inhibitor may be administered once a day (SID/QD), twice a day (BID), three times a day (TID), four times a day (QID), or more, so as to administer an effective amount of the Hsp90α inhibitor to the subject, where the effective amount is any one or more of the doses described herein.

In various embodiments of the methods described herein, the therapeutic composition comprises an inhibitor of Hsp90α and a targeting element that targets markers on the surface of cancer cells. Markers on the surface of cancer cells that may be targeted by the targeting elements of the compositions described herein include but are not limited to 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNTO888, CTLA-4, DR5, EGFR, EGFRVIII, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-Rα, PDL192, phosphatidylserine, prostatic carcinoma cells, RANKL, RON, ROR1, ROR2, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2 or vimentin. Other antigens specific for cancer will be apparent to those of skill in the art and may be used in connection with alternate embodiments of the invention.

Pharmaceutical Compositions

In various embodiments, the present invention provides pharmaceutical compositions including a pharmaceutically acceptable excipient along with a therapeutically effective amount of an inhibitor of Hsp90α, so as to treat, inhibit, prevent metastasis of and/or reduce severity of HIF-1α-overexpressing cancer in subjects in need thereof. In some embodiments, the inhibitors of Hsp90α include but are not limited to any one or more of small molecule, a peptide, an antibody or a fragment thereof or a nucleic acid molecule. In various embodiments, the inhibitor targets the F-5 epitope of Hsp90α. In an embodiments, the inhibitor is a nucleic acid molecule (for example, an siRNA) that targets Lys-270, Lys-277 or a combination thereof, of Hsp90α. In another embodiment, the inhibitor is a monoclonal antibody that specifically recognizes and binds Hsp90α. In an embodiment, the antibody is 1G6-D7 monoclonal antibody which binds the amino acid sequence TKPIWTRNP (SEQ ID NO: 1) in Hsp90α. In another embodiment, the antibody is 5C4-D4 monoclonal antibody which binds the amino acid sequence VKHFSVEGQ (SEQ ID NO: 2) in Hsp90α.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, parenteral or enteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the antibodies are administered by injection, either intravenously or intraperitoneally. Methods for these administrations are known to one skilled in the art.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Before administration to patients, formulants may be added to the antibodies (such as the Hsp90α inhibitors described herein). A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxyethyl starch and carboxymethylcellulose, or mixtures thereof. "Sugar alcohol" is defined as a $C_4$ to $C_8$ hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

In some embodiments, polymers as formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Additionally, antibodies (such as Hsp90α specific antibodies described herein) can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546 which are all hereby incorporated by reference in their entireties. Preferred polymers are polyoxyethylated polyols and polyethylene glycol (PEG). PEG is soluble in water at room temperature and in some embodiments, has an average molecular weight between 1000 and 40,000, between 2000 and 20,000, or between 3,000 and 12,000. In some embodiments, PEG has at least one hydroxy group, such as a terminal hydroxy group. The hydroxy group may be activated to react with a free amino group on the inhibitor. However, it will be understood that the type and amount of the reactive groups may be varied to achieve a covalently conjugated PEG/antibody of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a molecular weight in the same range as PEG. The structure for POG is shown in Knauf et al., 1988, J. Bio. Chem. 263:15064-15070 and a discussion of POG/IL C 2 conjugates is found in U.S. Pat. No. 4,766,106, both of which are hereby incorporated by reference in their entireties.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., Drug Delivery Systems (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The dosage and mode of administration will depend on the individual. Generally, the compositions are administered so that antibodies are given at a dose between 1 mg/kg and 20 mg/kg, between 20 mg/kg and 10 mg/kg, between 1 mg/kg and 7 mg/kg. In some embodiments, it is given as a bolus dose, to increase circulating levels by 10-20 fold and for 4-6 hours after the bolus dose. Continuous infusion may also be used after the bolus dose. If so, the antibodies may be infused at a dose between 5 mg/kg/minute and 20 mg/kg/minute, or between 7 mg/kg/minute and 15 mg/kg/minute.

Kits of the Invention

The invention also provides a kit to treat, inhibit, prevent metastasis of and/or reduce severity of HIF-1α-overexpressing cancer in a subject in need thereof. The kit comprises a pharmaceutical composition including a pharmaceutically acceptable excipient along with a therapeutically effective amount of an inhibitor of Hsp90α, so as to treat, inhibit, prevent metastasis of and/or reduce severity of HIF-1α-overexpressing cancer in subjects in need thereof. In one embodiment, the cancer is lung cancer. In another embodiment, the cancer is breast cancer. In some embodiments, the inhibitors of Hsp90α include but are not limited to any one or more of small molecule, a peptide, an antibody or a fragment thereof or a nucleic acid molecule. In various embodiments, the inhibitor targets the F-5 epitope of Hsp90α. In an embodiments, the inhibitor is a nucleic acid molecule (for example, an siRNA) that targets Lys-270, Lys-277 or a combination thereof, of Hsp90α. In another embodiment, the inhibitor is a monoclonal antibody that specifically recognizes and binds Hsp90α. In an embodiment, the antibody is 1G6-D7 monoclonal antibody which binds the amino acid sequence TKPIWTRNP (SEQ ID NO: 1) in Hsp90α. In another embodiment, the antibody is 5C4-D4 monoclonal antibody which binds the amino acid sequence VKHFSVEGQ (SEQ ID NO: 2) in Hsp90α.

The kit is an assemblage of materials or components, including at least one of the inventive compositions. Thus, in some embodiments the kit contains a composition including the catalytically active antibody having sialidase activity produced by the methods described herein, as described above.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as so treat, inhibit, reduce the symptoms of and/or promote prophylaxis of autoimmune diseases and/or cancer in a subject. Optionally, the kit also contains other useful components, such as, measuring tools, diluents, buffers, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a bottle used to contain suitable quantities of an inventive composition containing the catalytically active antibody having sialidase activity produced by the methods described herein. The packaging material generally has an external label which indicates the contents and/or purpose of the kit and/or its components.

EXAMPLES

The inventors determine which isoform, Hsp90α and Hsp90β, and what location of these proteins, extracellular or intracellular, are directly responsible for cancer cell migration, invasion and tumor formation. The inventors also identify the molecular basis that determines the extracellular function of Hsp90 proteins. Finally, newly developed monoclonal antibodies, 1G6-D7 and 5C4-D4 that target the key epitope of cancer cell-secreted Hsp90α, show a strong therapeutic potential for treatment of cancer.

Example 1

Experimental Methods

Eight human breast cancer cell lines and one control (untransformed) mammary epithelial cell line (FIG. S1A) were used. All the cells were cultured in DMEM medium supplemented with 10% fetal bovine serum (FBS), as well as ATCC-suggested media for some of the cell lines. No significant differences were observed in proliferation and invasion assays using either DMEM or specific media such as McCoy's 5A. Prior to experiments, the cells were deprived of serum and incubated under serum-free conditions for 16 hours. These cells were then subjected to cell growth curve, cell motility and cell invasion assays. Anti-Hsp90α specific antibody for Western analysis was purchased from Calbiochem (Darmstadt, Germany). Anti-Hsp90β specific antibody (neutralization and Western blot) was from StressMarq Biosciences Inc. (Victoria, BC Canada). These antibodies do not cross react between Hsp90α and Hsp90β. Development of monoclonal antibodies, 1G6-D7 and 5C4-D4 is described herein. Colloidal gold beads were purchased from Sigma-Aldrich (St. Louis, Mich.). XL-10 Gold Ultra competent cells (XL-10 Gold) were from Stratagene (La Jolla, Calif.). pET system (pET15b) for protein production in *E. Coli* was purchased from Novagen (Madison. Wis.). Matrigel invasion chambers (354480) and protocols were from BD Biosciences (Bedford, Mass.).

Production of Monoclonal Antibodies

Antigen Preparation:

cDNA of the F-5 fragment was cloned into the pET-15b his-tag expression system (Novagen) and expressed in BL-21-codonPlus(DE3)-RP bacteria in response to IPTG induction. Affinity purified His-F-5 protein was subjected to thrombin digestion (RECOMT, Sigma) to remove the His tag and filtered/washed to return to isotonic conditions. His tag-free F-5 (lane 6) was further purified through a molecular sieve column by FPLC and tested for pro-motility activity on primary human keratinocytes and dermal fibroblasts using the colloidal gold migration assay. The highly purified and functional F-5 protein was used for immunization in mice Immunization:

Three mice were immunized with 150 mg of F-5 protein per injection. Following antiserum screening, one mouse (#1) was selected for fusion and monoclonal antibody-producing cell screening. The antisera showed reactivity with the F-5 antigen and majority of the positive clones were IgG type.

Pre- and Anti-Serum Tests:

Following the above ELISA screening, we tested the antisera from the three immunized mice using Western blot and neutralization (inhibition of F-5-stimulated human skin cell migration) assays. Antiserum from each of the three F-5 immunized mice strongly recognized F-5 proteins. Under normoxia (21% $O_2$), human dermal fibroblasts showed baseline migration and hypoxia (1% O2) promoted the migration. All three anti-sera but not pre-immune serum inhibited hypoxia-induced human dermal fibroblast migration.

Fusion and Screening:

The spleen cells of the mouse whose serum showed the strongest reaction in all three assays (i.e. ELISA, Western blot and inhibition of cell migration), was selected for fusion (with HL-1 myeloma cells) and subjected to sequential screening processes to obtain "mother" clones. We used ELISA to screen approximately 800 fusion clones, and narrowed down to 24 mother clones. These 24 clones were subjected to further ELISA and functional assay (i.e. inhibition of Hsp90α-triggered cell migration), leading to the four mother clones.

Isotype and Epitope Mapping:

Two hybridoma clones, 1G6-D7 and 5C4-D4 were finalized and cultured in HL-1 medium containing all necessary growth factors and nutrients until they have grown to ~2.5×10$^6$ cells/ml density. The cell cultures were shifted to serum-free medium and incubated for additional 5 days. The conditioned media were collected and antibodies purified by protein-G Sepharose affinity chromatography. We found that the conditioned medium usually contained 3-5 µg/ml of IgG.

Purified antibodies from the two clones were subjected to isotype mapping using the Mouse Monoclonal Antibody Isotyping kit (IsoStrip, Cat. No. 11493027001). We found that one mAb, 1G6-D7, is IgG1κ and the second mAb, 5C4-D4, is IgG2aκ. These two mAbs were sent to GenScript (Piscataway, N.J.) for epitope mapping. The epitopes for 1G6-D7 and 5C4-D4 were mapped at TKPIWTRNP (SEQ ID NO: 1) and VKHFSVEGQ (SEQ ID NO: 2), respectively, within the F-5 region.

Under the provisions of the Budapest Treaty on the International Recognition of the Deposit of Microorganisms for the Purposes of Patent Procedure, Applicant has deposited biological materials with the American Type Culture Collection (ATCC) on Aug. 30, 2018 comprising hybridoma 1G6-D7 under the accession number PTA-125207 and hybridoma 5C4-D4 under the accession number PTA-125208.

Lentiviral Systems for Up- or Down-Regulation of Target Genes

The pRRLsinh-CMV system was used to overexpress exogenous Hsp90 genes. The pHR-CMV-puro RNAi delivery system was used to deliver shRNAs against Hsp90α, GGAAAGAGCTGCATATTAA (SEQ ID NO: 3) (sense) and Hsp90β, GCATCTATCGCATGATCAA (SEQ ID NO: 4) (sense).

CRISPR-Cas9 (Plasmids and Transfection) Knockout of Hsp90α and Hsp90β Genes

We utilized the previously reported guide RNA (gRNA) synthesis protocol (Mali et al., 2013 *Science* 339, 823-826). First, we identified all 23 bp genomic sites according to the form 5'-N20NGG-3' near the target site of human Hsp90α gene (Gene ID:3320) and human Hsp90β gene (Gene ID:3326) we selected the following genomic site: 5'-GAC- CCAAGACCAACCGATGGAGG-3' (SEQ ID NO: 5) (Hsp90α) or 5'-GCTGATCTCATAAATAATTTGGG-3' (SEQ ID NO: 6) (Hsp90β) for synthesizing the gRNA. Then, the 5'-20 bp of the selected target sequence, i.e. 5'-GAC-CCAAGACCAACCGATGG-3' (SEQ ID NO: 7) (Hsp90α) or 5'-GCTGATCTCA TAAATAATTT-3' (SEQ ID NO: 8) (Hsp90β) was incorporated (italicized) into a 455 bp DNA fragment that bears all components necessary for gRNA expression, i.e. a U6 promoter+target sequence+guide RNA scaffold+termination signal as follows: TGTA-CAAAAAAGCAGGCTTTAAAGGAACCAATTCAGTC-GACTGGATCCGGTACC AAGGTCGGGCAG-GAAGAGGGCCTATTTCCCATGATTCCTTCATATTT-GCATATAC GATACAAGGCTGTTAGAGAGATAATTA-GAATTAATTTGACTGTAAACACAAAGA TATTAGTA-CAAAATACGTGACGTAGAAAGTAATAATTTCT-TGGGTAGTTTGCAGT TTTAAAATTATGTTTTAAAATGGACTATCATATGCT-TACCGTAACTTGAAAGTAT TTCGATTTCTTGGCTT-TATATATCTTGTGGAAAGGACGAAACACCGAC-CCAAGACC AACCGATGG (SEQ ID NO: 9) (Hsp90α) or GCTGATCTCATAAATAATTT(Hsp90β)GTTTTA-GAGCTAGAAATAGCAAGTTAAAATA AGGCTAGTC-CGTTATCAACTTGAAAAAGTGGCACCGAGTCGGT-GCTTTTTTTCTA GACCCAGCTTTCTTGTACAAAGTTGGCATTA (SEQ ID NO: 10). The entire DNA fragment was synthesized as guide Block (gBlock) by Integrated DNA Technologies, Inc. (Coraville, Iowa). For construction of the gRNA plasmid, the gBlock was amplified by PCR using primers (gRNA-block-EcoRI (F): GCGGAATTCTGTACAAAAAAGCA-GGC (SEQ ID NO: 11) and gRNA-block-EcoRI(R): GCG-GAATTCTAATGCCAACTTTGTACA (SEQ ID NO: 12)). The PCR amplicons were purified and subjected to EcoRI digestion and subcloned into the PiggyBac vector using the EcoRI site on the vector.

Approximately $1 \times 10^6$ MDA-MB-231 cells were plated into each well in a 6-well plate, transfected with the gRNA construct and hCas9 plasmid using Lipofectamine® LTX & Plus Reagent (Life Technologies, Grand Island, N.Y.). hCas9 plasmid with G418-resistant gene, mPB transposase and PiggyBac vector with blasticidin S deaminase (BSD) resistant gene were kindly provided to us by Dr. Qilong Ying (USC Stem Cell Institute). 24 hours following transfection, the medium was replaced with fresh medium containing 10 μm/ml BSD and 2 μg/ml G418 and incubated for an additional 4-5 days. The cells were monitored daily. Drug-resistant clones were isolated following the drug selection by using the "ring cloning" technique and the cloned cells plated into 60-mm tissue culture dishes. After the cell clones were expanded, the levels of Hsp90 family proteins in the cells were analyzed by Western blot.

Preparation of Serum-Free Conditioned Medium

The detailed protocols for culturing cells, changing medium, time for incubation, collecting serum-free conditioned medium, concentrating and analyzing it by Western immunoblotting were as described previously (Cheng et al., 2008 *Mol Cell Biol* 28, 3344-3358).

Invasion Assay

We followed the basic procedures as described by the manufacturer's instruction from the BD BioCoat™ Matrigel Invasion Chamber (354480) (BD Biosciences, Bedford, Mass.). The Corning Biocoat Matrigel Invasion Chamber (Cat#354480) was used in invasion studies. Serum-starved $2 \times 10^4$ cells in 0.5 ml of serum-free medium were seeded onto cell culture inserts in a 24-well tissue culture plate. Each insert had 0.3 square centimeters surface area and 8 micron pore size PET membrane covered with Matrigel matrix (a solubilized basement membrane preparation from EHS mouse sarcoma). In the lower chamber, 10% FBS containing DMEM medium was used as the chemoattractant. Using sterile forceps and in a cell culture hood, the inserts were carefully transferred to the wells containing the chemoattractant, avoiding any air bubbles. The entire setting was incubated under 5% $CO_2$ at 37° C. for 22 hours. On the following day, non-invaded cells were removed from the top chamber of the inserts by scrubbing with cotton swabs. The invaded cells at the bottom surface of the inserts were fixed with 100% methanol and stained with crystal violet (1%, for 2 min.). The inserts were washed twice with distilled water to remove excess stain and allowed to air dry. They were then visualized under the microscope (Zeiss Imager. A2) at 10× magnification under bright field. Invaded cells were photographed in different fields using the Axiovision software and five microscopic fields per insert were counted. The % invasion was calculated as per the formula:

$$\% \text{ Invasion} = \frac{\text{Number of cells invaded}}{\text{Total number of cells seeded}} \times 100$$

Production and Purification of Recombinant Hsp90 (Hsp90α and Hsp90β and Mutants)

pET15b-Hsp90 constructs were transformed into BL21-codonPlus (DE3)-RP competent cells (Stratagene) following the manufacturer-provided protocol. Protein synthesis was induced by the addition of 0.25 mM IPTG (Sigma, 15502-09) to the bacterial culture after reaching the log phase of growth (O.D.≈0.8) and incubated for an additional five hours at 25° C. The bacteria were processed according to the pET-15b system manufacturer's instructions (EMD biosciences, Inc., San Diego Calif.). The his-tagged proteins were first partially purified by Ni-NTA column with the HisBind purification kit (EMD biosciences, Inc.). The proteins were concentrated in Amicon Ultra centrifugal columns (10× or 50×) (Millipore, Billerica, Mass.) to ~4 ml, filtered (0.22 μm) prior to loading onto a Superdex-200 or 75 HiLoad gel filtration column (GE healthcare, Piscataway, N.J.) and separated by Fast Protein Liquid Chromatography (FPLC). The peptides were eluted by the DPBS buffer (1 ml/min), concentrated to 1 mg/ml and stored in 10% glycerol-DPBS at −80° C.

Circular Dichroism (CD) Spectroscopy

Hsp90α, Hsp90β and mutant variants were exchanged into 5 mM $K_2HPO_4/KH_2PO_4$, pH 7.4, solution by four ultrafiltration-dilution cycles (1:10 dilution). CD measurements were carried out at 25° C. on a JASCO J-810 spectropolarimeter by acquiring spectra of 10 mM samples from 190 to 260 nm in a quartz cell of 1 mm path length. 32 scans, recorded in 0.1 nm steps at a rate of 50 nm/min with a 0.1 nm bandwidth and a 0.5 s integration time, were accumulated. Spectra were corrected for solvent contributions. The observed ellipticity in millidegrees was converted to the mean residue ellipticity.

Statistical Analyses

Data are based on three independent experiments. Colloidal gold salt migration assay quantification was achieved by measuring the individual tracks of 20 randomly selected individual cells per experimental condition, where each condition in an experiment was repeated for at least three times. The data are presented as mean±s.d. Matrigel invasion assay quantification was achieved by measuring five randomly selected fields per experimental condition. Statistical differences were evaluated using the two-tailed Student t-test for comparisons of two groups, or analysis of variance for comparisons of more than two groups. p<0.05 was considered significant.

Example 2

Figure 1B:
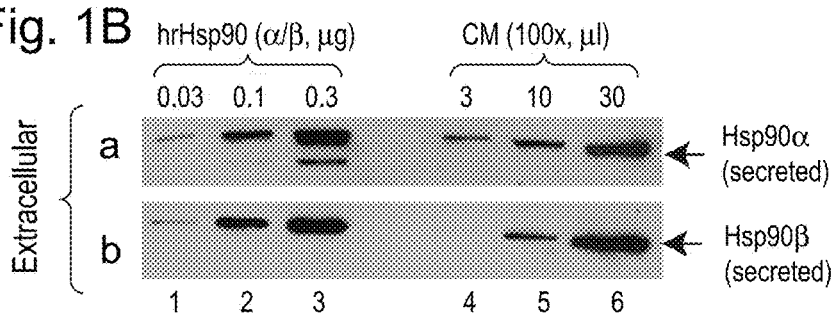
Figure 1C:
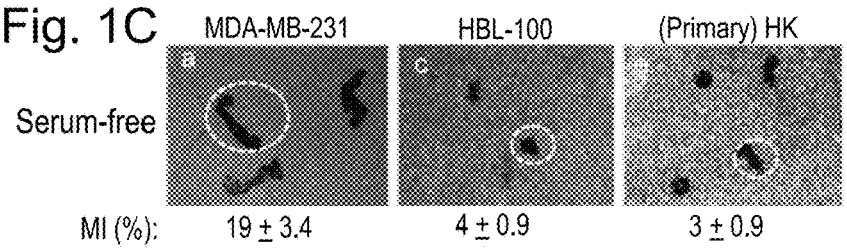
Figure 1D:
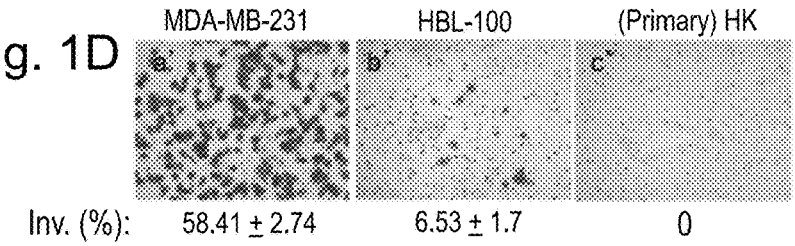

Hsp90β for Survival and Hsp90α for Constitutive Motility and Invasiveness of Tumor Cells We first screened eight commonly studied breast cancer cell lines that are ER$^+$, HER2$^+$ or triple negative, to identify the most invasive cell line and use it as the cell model. The MDA-MB-231 cells showed six to ten fold higher invasiveness than the rest of the cell lines with a non-transformed mammary epithelial cell line, HBL-100 (Gaffney, 1982 *Cell Tissue Res.* 227: 563-568), as the baseline control. MDA-MB-231 cells maintain a steady-state level of Hsp90 protein around 3.5% of the total cellular proteins, significantly higher than the 1-2% in normal cells (Sahu et al., 2012 *Mol Biol Cell* 23, 602-613). We examined the inside and outside pools of Hsp90α and Hsp90β using antibodies that do not crossreact between the antigens. As shown in FIG. 1A, increasing amounts of Hsp90α (panel a, lanes 4-6) and Hsp90β (panel b, lanes 4-6) were detected in increasing volumes of the cell lysates, with purified recombinant Hsp90α (panel a, lanes 1-3) and Hsp90β (panel b, lanes 1-3) proteins included as controls. We also detected constitutive secretion of Hsp90α and Hsp90β from serum-free conditioned medium of the cells (FIG. 1B, panels a and b, lanes 4 to 6). As demonstrated in FIG. 1C, MDA-MB-231 cells maintained a constitutive and saturated motility even under the serum-free conditions (panel a), since the addition of serum showed little further enhancement (panel b). In comparison, serum-starved normal human mammary epithelial cell line, HBL-100 (panels c and d) or primary human keratinocyte (panels e and f) showed little basal motility in the absence of serum (panels c and e) and exhibited dramatically enhanced motility in the presence of serum (panels d and f). Likewise, MDA-MB-231 cells were highly invasive, as defined by their ability to penetrate through a Matrigel barrier under serum-free conditions (FIG. 1D, panel a'). In contrast, the two normal cell lines showed little invasiveness under the similar conditions (panels b' and c'). Therefore, MDA-MB-231 cells satisfy the key parameters, namely, a HIF-1α-positive, LRP-1-positive and Hsp90α-secreting human breast cancer cell model.

We investigated whether Hsp90α or Hsp90β or both determine the intrinsic motility and invasiveness of the breast cancer cells in vitro. We chose to knockout Hsp90α and Hsp90β genes in MDA-MB-231 cells by the CRISPR-Cas9 technology. As shown in FIG. 2A, a significant number of the cells survived the drug selections for Hsp90α gene knockout (panel c vs. panels a and b). Almost all the cells that were subjected to drug selections for Hsp90β gene knockout stopped proliferation and detached (panel f vs. panels d and e).

The direct proof that Hsp90α gene was knocked out is presented in FIG. 2B. Two independent cell clones isolated from the survived cells showed complete absence of Hsp90α protein (panel a, lanes 3 and 4), in comparison to the parental MDA-MB-231 cells (lane 1). In comparison, knockdown of Hsp90α by a lentivirus-expressed shRNA against Hsp90α was included, in which a small amount of Hsp90α protein was detected (lane 2). In Hsp90α-knockout cell clones, we also noticed a slight increase in the level of Hsp90β protein (panel b, lanes 3 and 4, vs. lanes 1 and 2). As shown in FIG. 2C, the proliferative potential of both Hsp90α-knockout and Hsp90α-knockdown cells were indistinguishable from unperturbed parental MDA-MB-231 cells in either the absence or presence of serum. Furthermore, the Hsp90α knockout did not appear to alter the cellular signal transduction. Taking the EGFR signaling as an example, as shown in FIG. 2D, constitutive ERK1/2 phosphorylation was detected in both the parental and Hsp90α-knockout cells (panel d). TGFα- and EGF-stimulated p38 phosphorylation remained unchanged (panel e). The TGFα-, but not EGF-, stimulated Akt phosphorylation (S-473) was reduced in Hsp90α-knockout cells (panel f). This decrease is likely due to the fact that TGFα, but not EGF, stimulates Hsp90α secretion and the secreted Hsp90α activates Akt via an autocrine mechanism (Cheng et al., 2008 *Mol Cell Biol* 28, 3344-3358; Tsen et al., 2013 *Mol Cell Biol.*, 33:4947-4953). While Akt phosphorylation remained inducible by growth factor stimulation, the PRAS40 phosphorylation was constitutive (panel g), suggesting that Akt may not be the only upstream kinase that directly phosphorylates PRAS40 (at threonine-246), as it was suggested previously (Kovacina et al. 2003 *J Biol Chem* 278: 10189-10194). As expected, however, secreted Hsp90α was no longer detectable from the conditioned medium of the Hsp90α-knockout cells, due to depletion of its intracellular storage (FIG. 2E, panel g, lane 5 vs. lane 4). In contrast, Hsp90α-knockout cells still secreted Hsp90β as the parental control cells (FIG. 2E panel h, lane 5 vs. lane 4). Taken together, the above findings suggest that Hsp90β alone is sufficient for the intracellular chaperone duties in the absence of Hsp90α, whereas Hsp90α alone is not in the absence of Hsp90β. These cellular findings are consistent with those in mouse genetic studies that Hsp90β gene knockout caused embryonic lethality (Voss et al., 2000 *Development* 127, 1-11), whereas Hsp90α-knockout mice survived and developed normally (Grad et al., 2010 *PLoS One* 5, e15770; Imai et al., 2011 *Proc Natl Acad Sci USA* 108, 16363-16368).

While depletion of Hsp90α did not affect the cell survival and growth, the Hsp90α-knockout MDA-MB-231 cells have lost their intrinsic motility and invasiveness in vitro. As shown in FIG. 2F, both Hsp90α-knockdown (panel b) and Hsp90α-knockout (panels c and d) cells became non-motile, in comparison with the parental counterparts (panel a), as measured by single cell's Migration Index (MI, %). This motility defect was due specifically to Hsp90α depletion, instead of some overriding cell toxicity or general harmful effect on the cell's basic machinery by the gene knockdown or knockout, since addition of serum could still stimulate migration of the same cells, similar to normal control cells (panels f to h). Similarly, as shown in FIG. 2G, the Hsp90α-knockdown (panel b) and Hsp90α-knockout (panels c and d) cells were no longer able to invade through the Matrigel, which imitates a tissue basement membrane barrier. These findings indicated that Hsp90β, which was still present in the Hsp90α-knockout cells, was unable to support the cells' ability to migrate and invade under serum-free conditions. Moreover, this failure by Hsp90β was not due to the reduced total levels of Hsp90 proteins in these cells (FIG. 3).

We found that the Hsp90α-knockout tumor cells completely lost their ability to invade a Matrigel in vitro and to form tumors at mammary fat pad (an orthotopic site for breast cancer studies such as the host-tumor interactions on tumor biology and therapeutic responses) and metastasize to lung in mice. As shown in FIG. 2H, neither of the Hsp90α-knockout cell clones were able to invade (panels b and c), unlike their highly invasive parental cells (panel a). Similarly, the parental LM2-4175 cells injected into the mammary fat pad of nude mice formed tumors in four of the five mice within four weeks (FIG. 2I, panel a). In contrast, only one small tumor was found in one of the five mice in the group injected with the Hsp90α-knockout cells (panels c). The tumors were excised and measured for tumor volume (TV) (panels b and d). Histological analysis of the excised tumors or tissue with corresponding sizes from the injection site confirmed a dramatic reduction of tumor-forming ability for Hsp90α-knockout cells versus their parental counterpart (panel g vs. panel e). Furthermore, the tumors formed by parental LM2-4175 (lung-metastasizing breast cancer cell line) cells metastasized into the lung (panel f). In contrast, we did not detect tumor lung metastasis from the mice injected with Hsp90α-knockout cells (panel h).

Example 3

Secreted Hsp90α is Responsible for Tumor Cell Motility and Invasiveness

We investigated whether it is the intracellular or the secreted form of Hsp90α that is responsible for the tumor cell's motility and invasiveness. We carried out "inside-out" and "outside-in" gene rescue experiments using the Hsp90α-knockout cell lines. As shown in FIG. 3A, we exogenously expressed GFP-tagged wild type (wt) and the ATPase-defective mutant (D93N) Hsp90α genes (lanes 3 and 4 vs. lane 1). Independently, we also expressed the wild type Hsp90β gene in the Hsp90α-knockout cells, in order to replenish the amount of cytosolic Hsp90 proteins in such a way that the total amount of Hsp90, i.e. by Hsp90β alone, was the same as the combined amount of Hsp90α and Hsp90β in the parental cells. As shown in FIG. 3B, Hsp90α-knockout cells infected with lentivirus carrying the human Hsp90β gene exhibited increased expression of Hsp90β as determined by Western blot analysis with an anti-Hsp90β-specific antibody (panels c, lane 3 vs. lanes 1 and 2) The slightly increased Hsp90β in lane 2 (vs. lane 1) was due to the Hsp90α knockout. Blotting with a pan anti-Hsp90 antibody (labeling both Hsp90β and Hsp90α) showed that the total amount of Hsp90 in the Hsp90β-overexpressing Hsp90α-knockout cells was similar to the parental cells (panel d, lane 3 and lane 1). In contrast, the vector alone-infected Hsp90α-knockout cells showed a lower level of Hsp90 (i.e. with only the endogenous Hsp90β). The establishment of the Hsp90α-knockout cells that exogenously overexpress Hsp90α and Hsp90β allowed us to seek answers for whether Hsp90α or Hsp90β controls cancer cell motility and invasion.

Figure 3D:
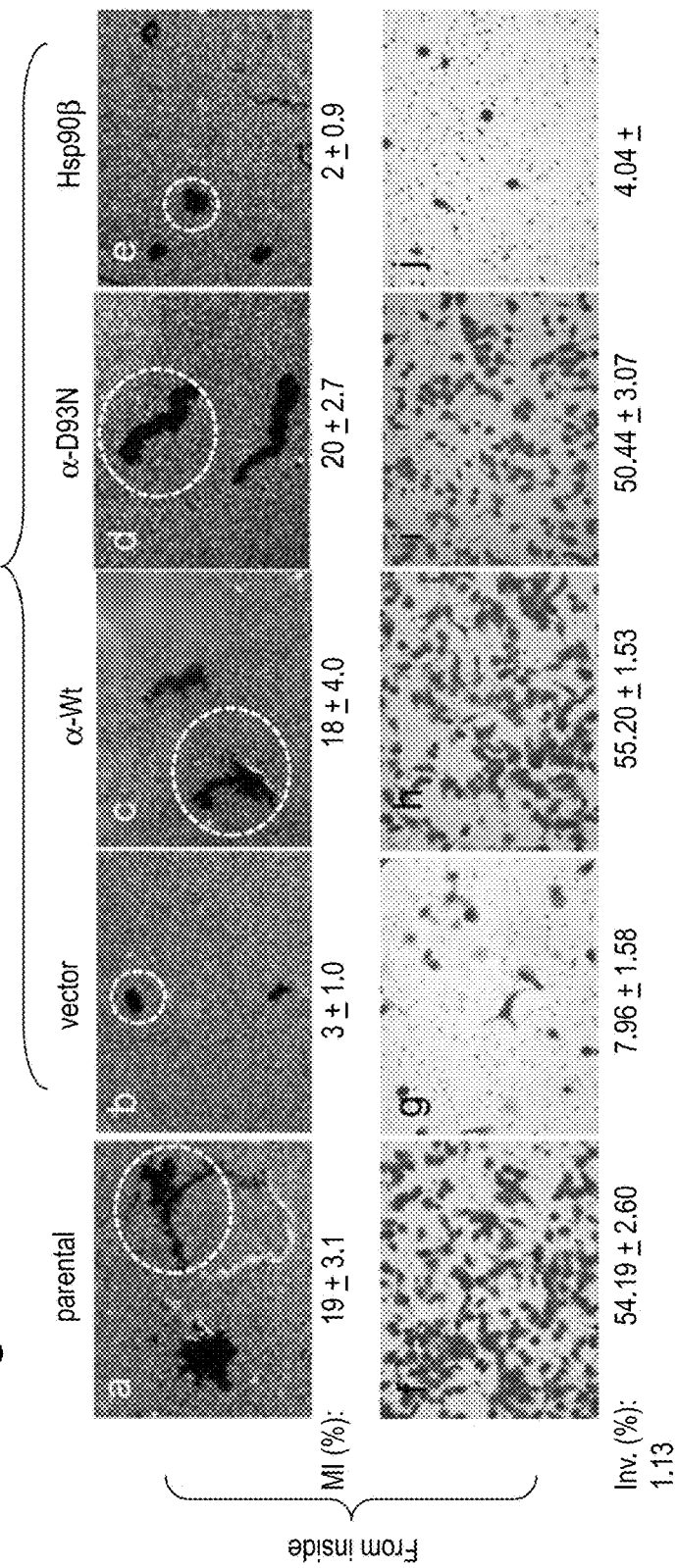
Figure 3G:
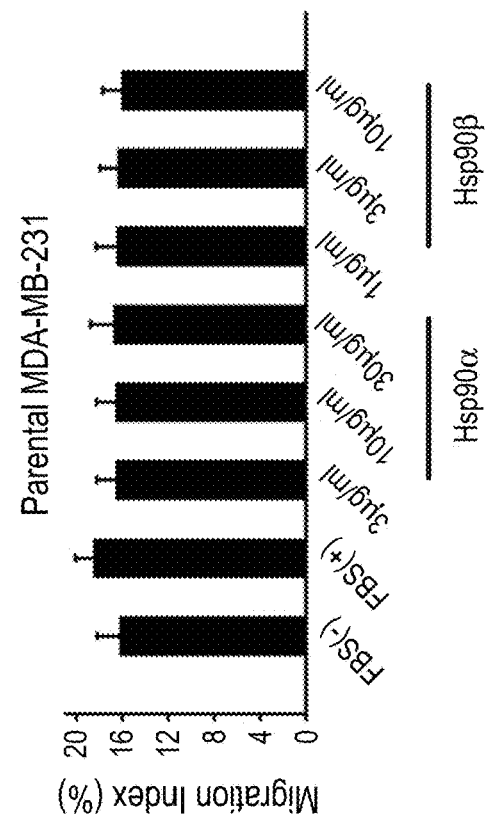
Figure 3F:
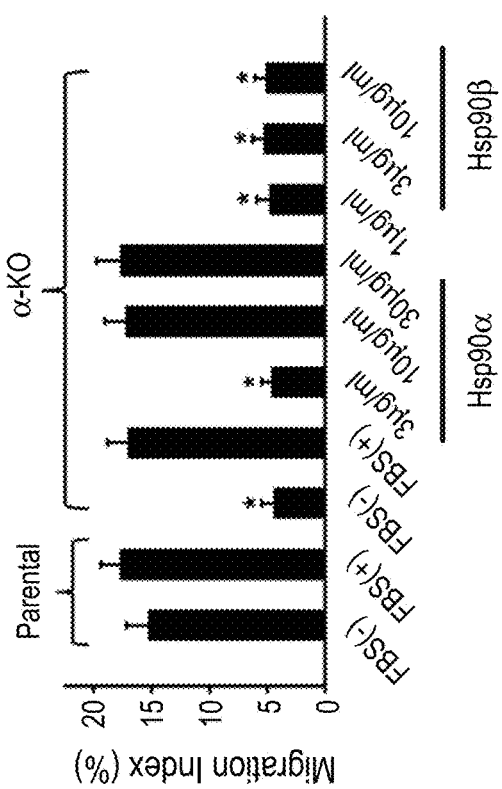
Figure 3H:
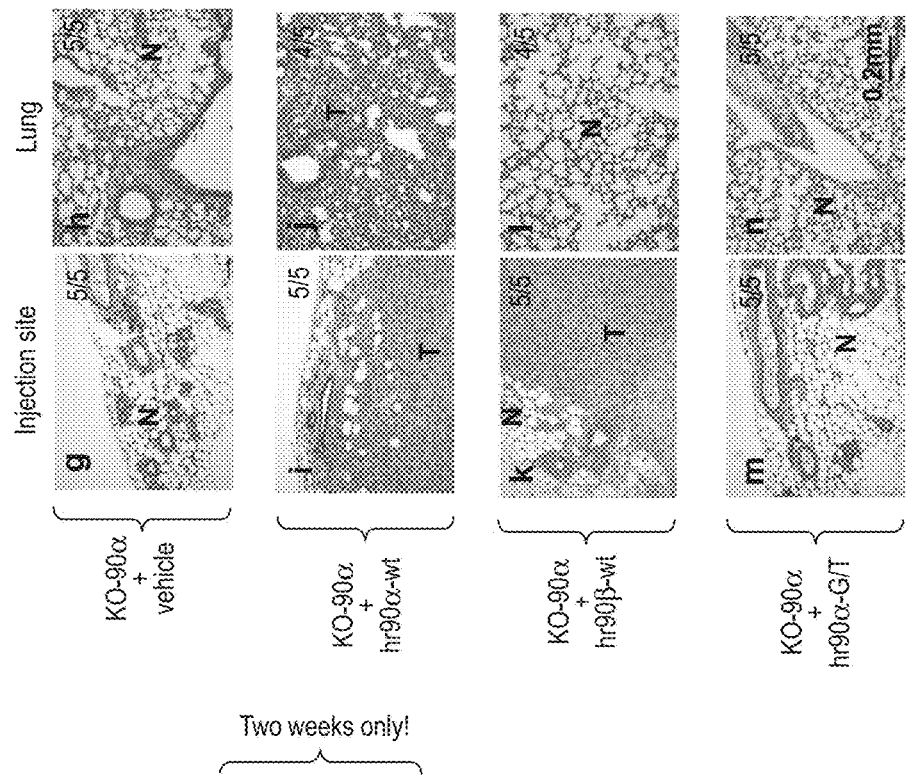

As shown in FIG. 3D, we found that overexpressed wild type and D93N mutant Hsp90α were capable of rescuing both the motility defect (panels c and d versus panels b) and the invasion defect (panels h and i versus panel g) in Hsp90α-knockout cells. These data suggest that the rescue by Hsp90α is via an ATPase-independent mechanism. In contrast, overexpression of Hsp90β was unable to correct either motility or invasion defect (panels e and j). The rescue was due to the extracellular action of secreted Hsp90α. As shown in FIG. 3E, the addition of recombinant Hsp90α protein to the Hsp90α-knockout cells was sufficient to restore their ability to migrate and invade (FIG. 3E, panels c' and g'). In contrast, recombinant Hsp90β protein was unable to do the same (panels d' and h'). The purity of the recombinant Hsp90α or Hsp90β proteins used for the above tests are shown in FIG. 3C (lanes 4 and 5). The dose-dependent effects of recombinant Hsp90α and Hsp90β proteins are shown in FIGS. 3F and 3G.

Figure 3I:
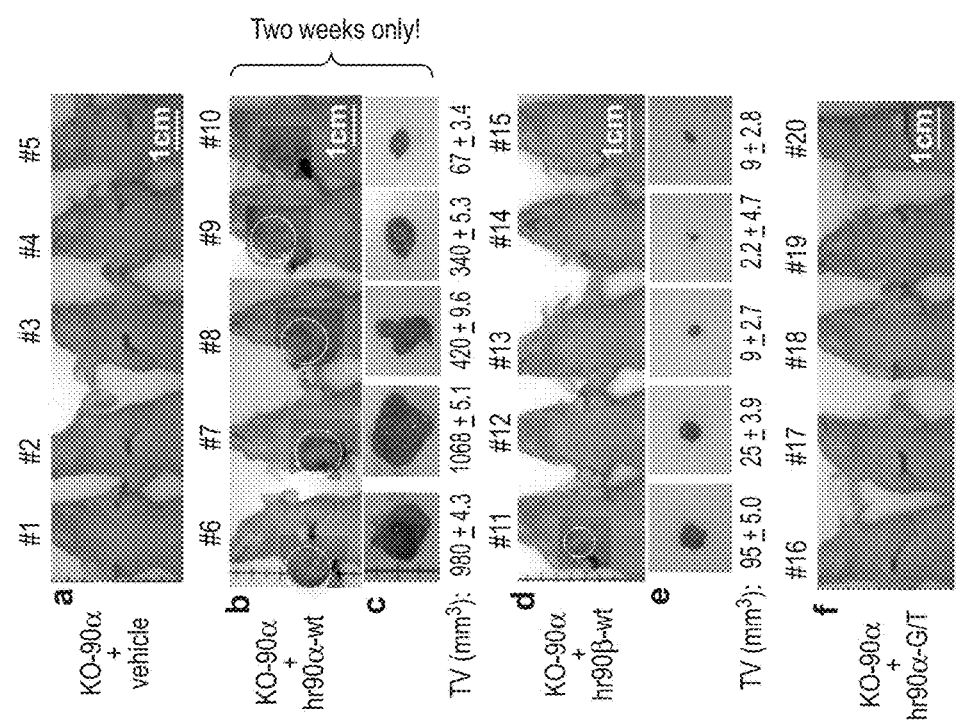

As shown in FIG. 3I, Hsp90α-knockout cells were unable to form tumors in all five mice (panel a). Co-injecting Hsp90α-knockout cells with recombinant Hsp90α protein was not only sufficient for Hsp90α-knockout cells to form tumors in five of the five mice in the group, but moreover the size of tumors in three of the five mice reached the IACUC limitation within two, instead of four, weeks, as needed by the parental tumor cells (panel b). Co-injection with recombinant Hsp90β protein also showed a rescue effect, but 50 to 100 fold weaker than recombinant Hsp90α based on the TV values of the excised tumors (FIG. 3I, panels c vs. e).

Example 4

Figure 4E:
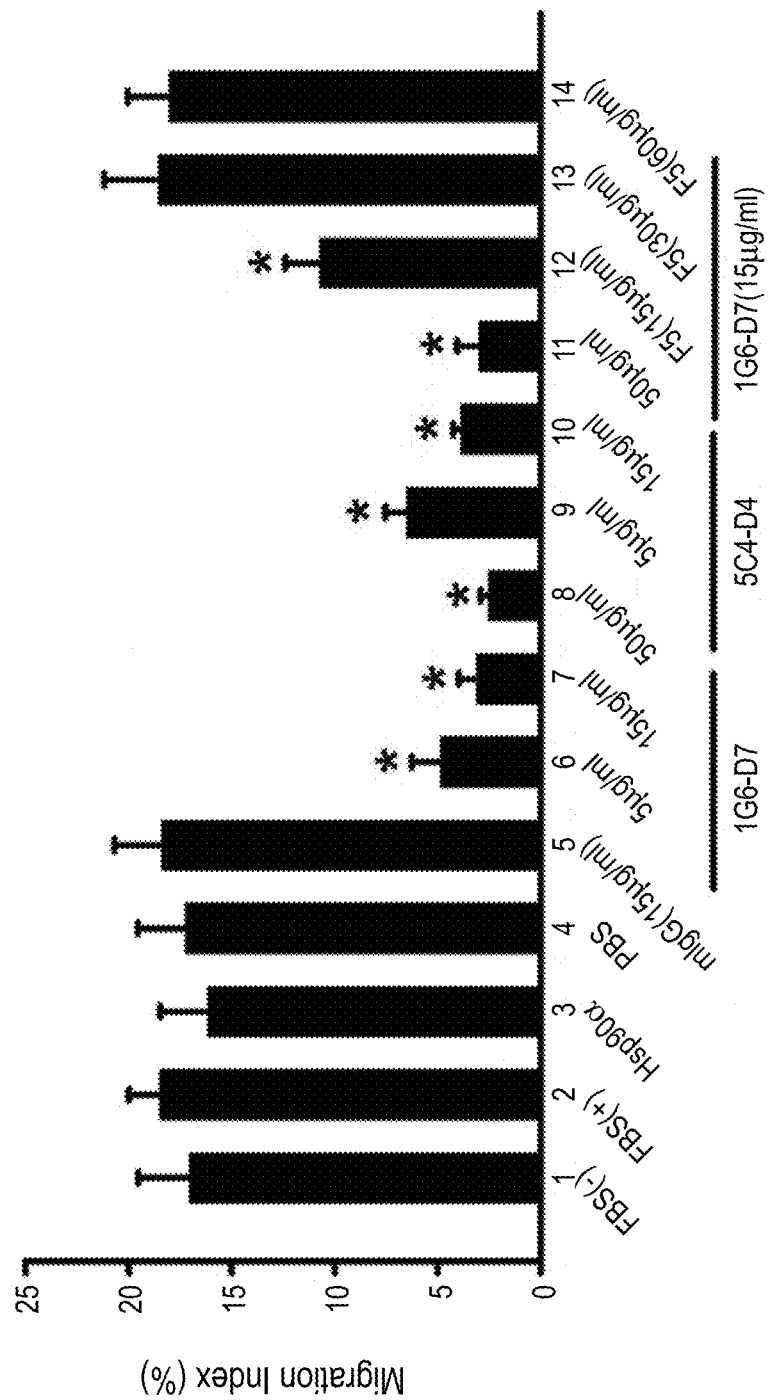

Monoclonal Antibodies, 1G6-D7 and 5C4-D4, Targeting the F-5 Region of Hsp90α Block Tumor Cell Motility and Invasion To further prove that it was the secreted, but not the intracellular, form of Hsp90α that was responsible for the constitutive motility and invasiveness of MDA-MB-231 cells, we have developed two lines of monoclonal antibodies targeting the 115-amino acid fragment, F-5, which is located at the linker region and the middle domain of Hsp90α (Cheng et al., 2011 *J Clin Invest* 121, 4348-4361). The immunogen preparation, immunization, screening and antibody epitope mapping, in which two hybridoma lines, 1G6-D7 and 5C4-D4, were cloned from screening more than 800 potential clones. As schematically shown in FIG. 4A, the epitopes for 1G6-D7 and 5C4-D4 in Hsp90α were mapped at the TKPIWTRNP (SEQ ID NO: 1) and VKHFSVEGQ (SEQ ID NO: 2) sequences within the F-5 region, respectively. Purified antibodies are shown in FIG. 4B (lanes 2 and 3) with known amounts of a commercial mouse IgG as control (lane 1). As shown in FIG. 4C, the addition of 1G6-D7 and 5C4-D4 blocked the constitutive motility of the MDA-MB-231 cells (panels c and d vs. panels a and b), in a dose-dependent manner (FIG. 4E). In contrast, anti-Hsp90β antibody showed little effect. The inhibition by 1G6-D7 and 5C4-D4 was due to specific binding of the antibodies to the F-5 region of Hsp90α, since the addition of excess amounts of recombinant F-5 peptide reversed the inhibitory effects of 1G6-D7 (panel f) and 5C4-D4 (panel g), in a dose-dependent manner (FIG. 4E).

Similarly, 1G6-D7 and 5C4-D blocked the invasion of parental MDA-MB-231 cells. As demonstrated in FIG. 4D, the addition of control IgG showed little effect (panel d' vs. panel a'). However, both 1G6-D7 (panels b' and c' vs. panels a' and d') and 5C4-D4 (panels e' and f' vs. panels a' and d') inhibited tumor cells invasion in a dose-dependent manner. The inhibition was specifically due to neutralization of the tumor cell-secreted Hsp90α, since the addition of recombinant F-5 reversed the inhibition by both 1G6-D7 (panels h' and i' vs. panel g') and 5C4-D4 (panels k' and l' vs. panel j'). Taken together, these results established the specific role for secreted Hsp90α in tumor cell motility and invasion and support the therapeutic uses of IG6-D7 and/or 5C4-D4 monoclonal antibodies.

Figure 4F:
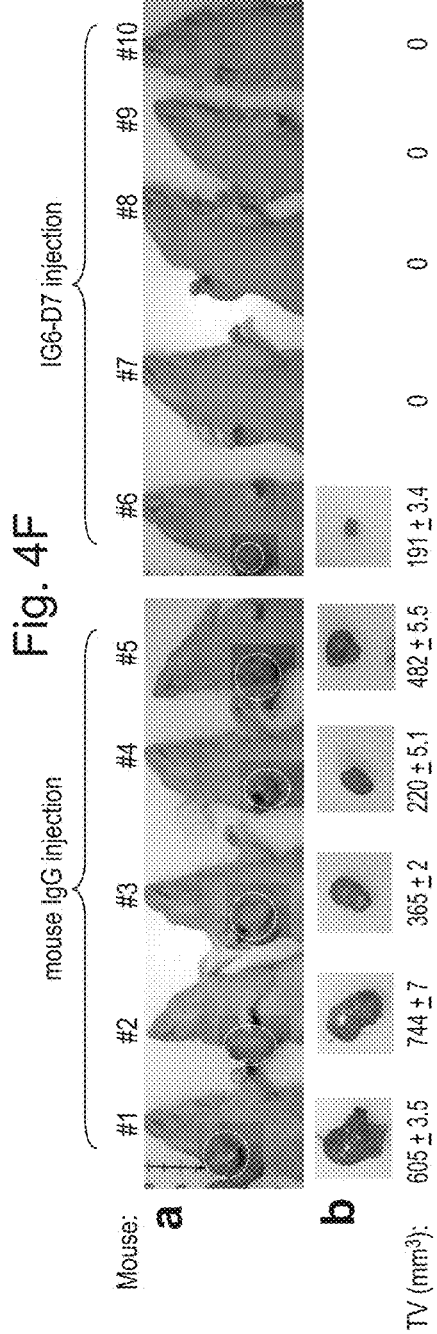

1G6-D7 blocked invasion of the parental LM2-4175 cells in a dose-dependent manner. The specificity of inhibition by 1G6-D7 was confirmed by the observation that the addition of excessive amounts of F-5 peptide reversed the inhibition by 1G6-D7. Intravenous injection of 1G6-D7 into the mice prevented the cells from forming tumors and metastasizing to lung. As shown in FIG. 4F, the parental LM2-4175 cells formed large tumors in five of the five mice (#1 to #5) that were injected with control mouse IgG (FIG. 4F, panel a).

Figure 4G:
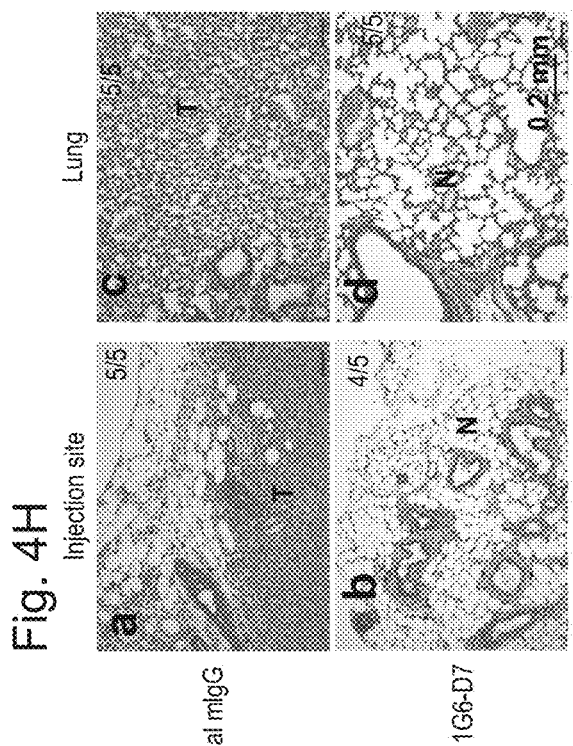
Figure 4H:
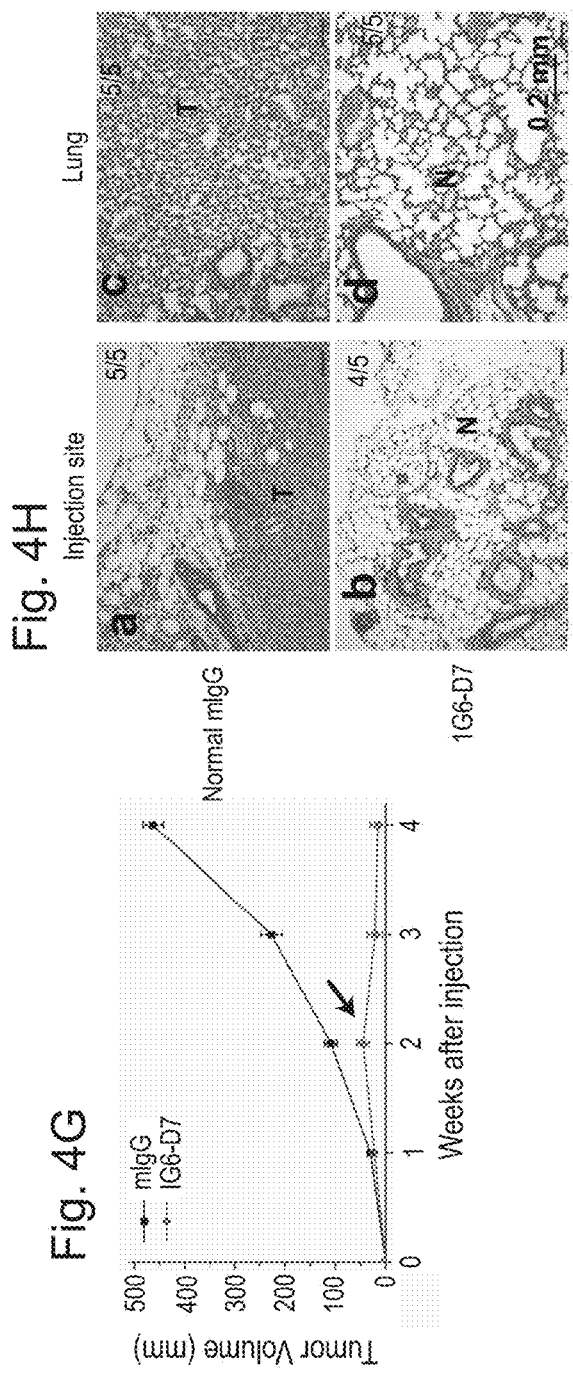

Injection of 1G6-D7, however, almost completely prevented tumor formation (#6 to #10). When the tumors on live mice from multiple experiments were calculated for average tumor volumes over the period of four weeks (FIG. 4G), it was noticed that tumors in 1G6-D7-injected mice tried to grow for the first two weeks, but ultimately failed to pick up the pace of their parental counterpart cells in mice injected with control IgG (arrow). Histological analysis confirmed lack of tumor formation in 1G6-D7-treated mice (FIG. 4H, panel b vs. panel a). All lung specimens excised from mice injected with control mouse IgG showed metastasized tumor cells (FIG. 4H, panel c). In contrast, no detectable tumor metastasis to lung was found in mice injected with 1G6-D7 (FIG. 4H, panel d).

Example 5

Lysine-270 and Lysine-277 within F-5 Region Determine the Extracellular Function of Hsp90α

Figure 5D:
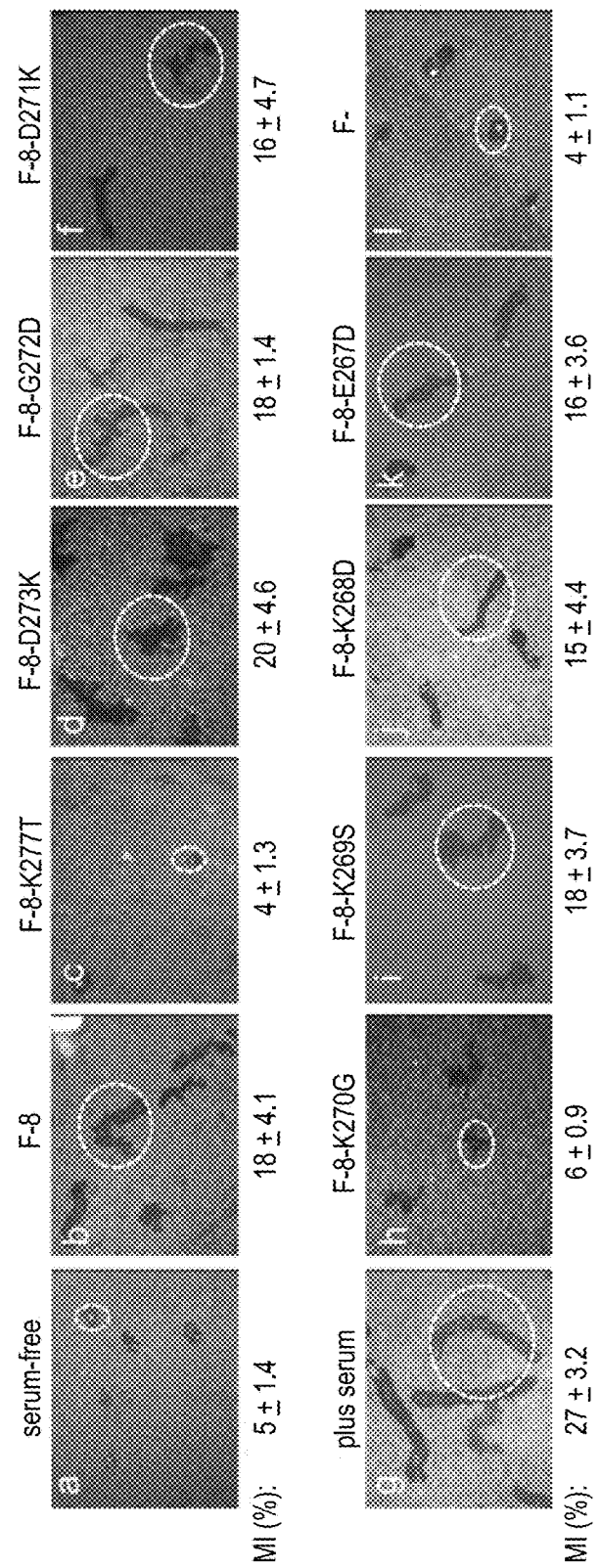

We investigated the molecular basis that determines the extracellular function of Hsp90 by focusing on the F-5 region. We carried out sequential mutagenesis to identify the essential amino acid residues. Deletion mutagenesis, as shown in FIG. 5A, allowed us to further narrow the pro-motility activity of the F-5 fragment down to a 54-amino acid fragment, F-6, and, then, to a 27-amino acid peptide, F-8. We then took advantage of the fact that Hsp90β, unlike Hsp90α, does not have any extracellular pro-motility and pro-invasion activities and compared the 27 amino acid sequence of F-8 with its corresponding sequence, F-8β, from Hsp90β. As shown in FIG. 5B, eight amino acids in F-8 are substituted with variant amino acids in F-8β. This finding suggested that the difference in extracellular function between Hsp90α and Hsp90β reside within the eight amino acid residues. To test this hypothesis, eight synthetic peptides with each of the eight amino acids in F-8 replaced with each of the corresponding amino acid residues from F-8β were screened for their ability to promote cell migration (FIG. 5C). Since MDA-MB-231 cells already show a saturated basal level of motility due to their constitutive secretion of Hsp90α and no longer exhibit a further increase in motility in response to exogenously added Hsp90α (FIG. 3G), we used primary human keratinocytes to test these peptides, because migration of these cells is strongly stimulated by recombinant Hsp90α protein, as previously shown (Cheng et al., 2011 *J Clin Invest* 121, 4348-4361). As shown in FIG. 5D, substitution of the lysine-270 (panel h) and the lysine-277 (panel c) dramatically reduced the pro-motility activity of the F-8 peptide (panel b vs. panel a). In contrast, other point mutations did not show significant effect on the pro-motility activity of F-8. As expected, F-8β did not show any detectable activity (panel 1). Quantitation of the migration is shown as a Migration Index (MI, %) below each of the migration images.

We tested if the mutant Hsp90α, Hsp90α-G/T, in which lysine-270 and lysine-277 were replaced by the corresponding residues, glycine and threonine, from Hsp90β, was able to promote tumor formation of Hsp90α-knockout cells. In contrast to the wild type Hsp90α protein (see FIG. 3I, panel b), we found Hsp90α-G/T failed to support tumor formation by Hsp90α-knockout cells (FIG. 3I, panel f). Histological analysis confirmed tumor formation at the mammary fat pad by Hsp90α-knockout cells supplemented with wild type Hsp90α or wild type Hsp90β protein (FIG. 3J, panels I and k). However, only co-injected Hsp90α (FIG. 3J, panel j), but not Hsp90β (FIG. 3J, panel 1), protein was able to drive Hsp90α-knockout cells to metastasize to the lung in four of all five mice (FIG. 3J, panel j). In contrast, we did not detect tumor formation and lung metastasis by either Hsp90α-knockout cells alone (FIG. 3J, panels g and h) or the same cells supplemented with the Hsp90α-G/T mutant protein (FIG. 3J, panels m and n). Taken together, the above findings indicate that lysine-270 and lysine-277, instead of the ATPase, determine the extracellular tumorigenic activity of Hsp90α and present the site for potential therapeutic targeting.

Figure 6A:
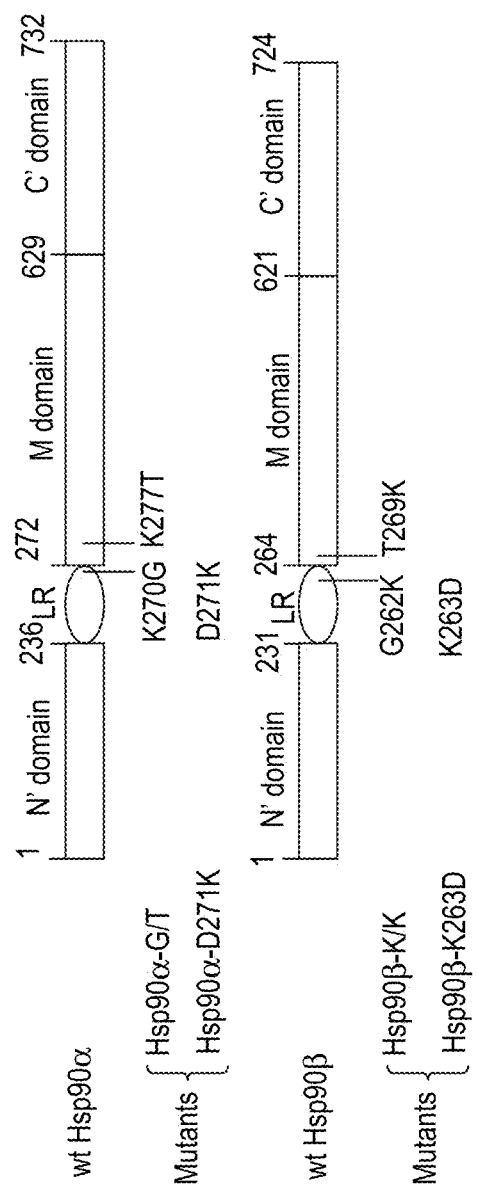
FIG. 6A to FIG. 6F depict, in accordance with an embodiments of the invention, Lysine-270 and Lysine 277 differentiate Hsp90α from Hsp90β and convert Hsp90β to function like Hsp90α.
Figure 6B:
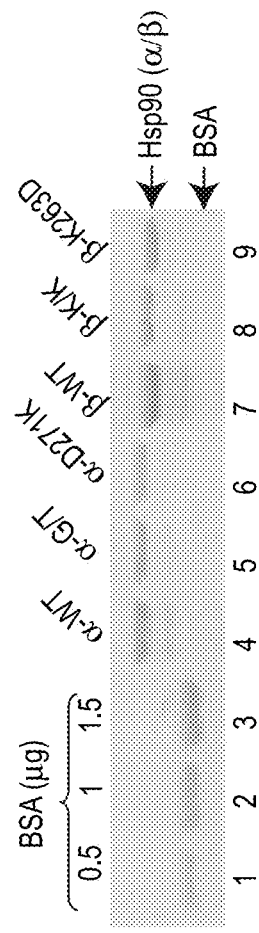

Mutagenesis study in the full-length Hsp90 genes was carried out to show that Lysine-270 and Lysine-277 define the molecular basis for the extracellular non-chaperone function of Hsp90 family of proteins. As schematically shown in FIG. 6A, we substituted the lysine residues in full-length Hsp90α with the two corresponding residues, i.e. glycine-262 and threonine-269 from Hsp90β, to create the Hsp90α-G/T mutant. In reverse, we replaced the glycine-262 and threonine-269 in full-length Hsp90β gene with lysine residues, to create the Hsp90β-K/K mutant. Two additional non-specific mutants, Hsp90α-D271K and Hsp90β-K263D, were included as negative controls. Six purified wild type and mutant proteins of full-length Hsp90α and Hsp90β are as shown in FIG. 6B (lanes 4 to 7). We then analyzed the secondary structural profiles of Hsp90α, Hsp90β, and their mutant proteins through computer modeling and circular dichroism (CD). The Hsp90α structure consists of three domains: the ATPase-containing N-terminal domain (NTD) is connected by a highly charged and unstructured linker region to the middle domain (MD), which is followed by the C-terminal dimerization domain (CTD). Lys-270 and Lys-277 are located in the linker region and, therefore, do not affect global protein structure. This is further supported by the results of CD analysis. We found that the CD spectra of Hsp90α and Hsp90β were characteristic of folded proteins containing a mix of secondary structure elements. Hsp90β exhibited a slightly lower ellipticity at 222 nm than Hsp90α, revealing a higher helical content. The mutant variants of each Hsp90α and Hsp90β were indistinguishable from the wild-type proteins. The mutations did not affect global protein structure but modulated the local structure of this dynamic linker region. Thus, we postulated that glycine-270 and threonine-277 substitutions in Hsp90α specifically nullify its function and, in reverse, the lysine-262 and lysine-269 replacements in Hsp90β will convert Hsp90β to an Hsp90α-like molecule that is capable of promoting tumor cell motility and invasion.

Figure 6C:
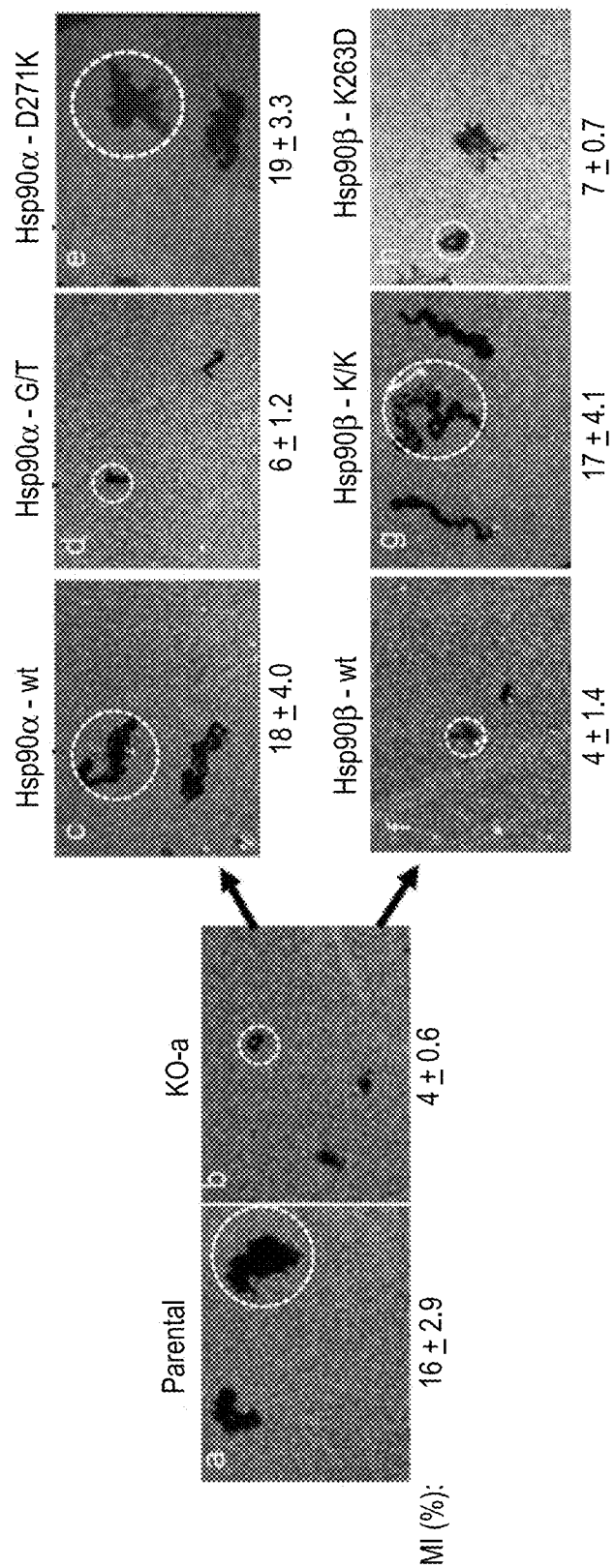
Figure 6D:
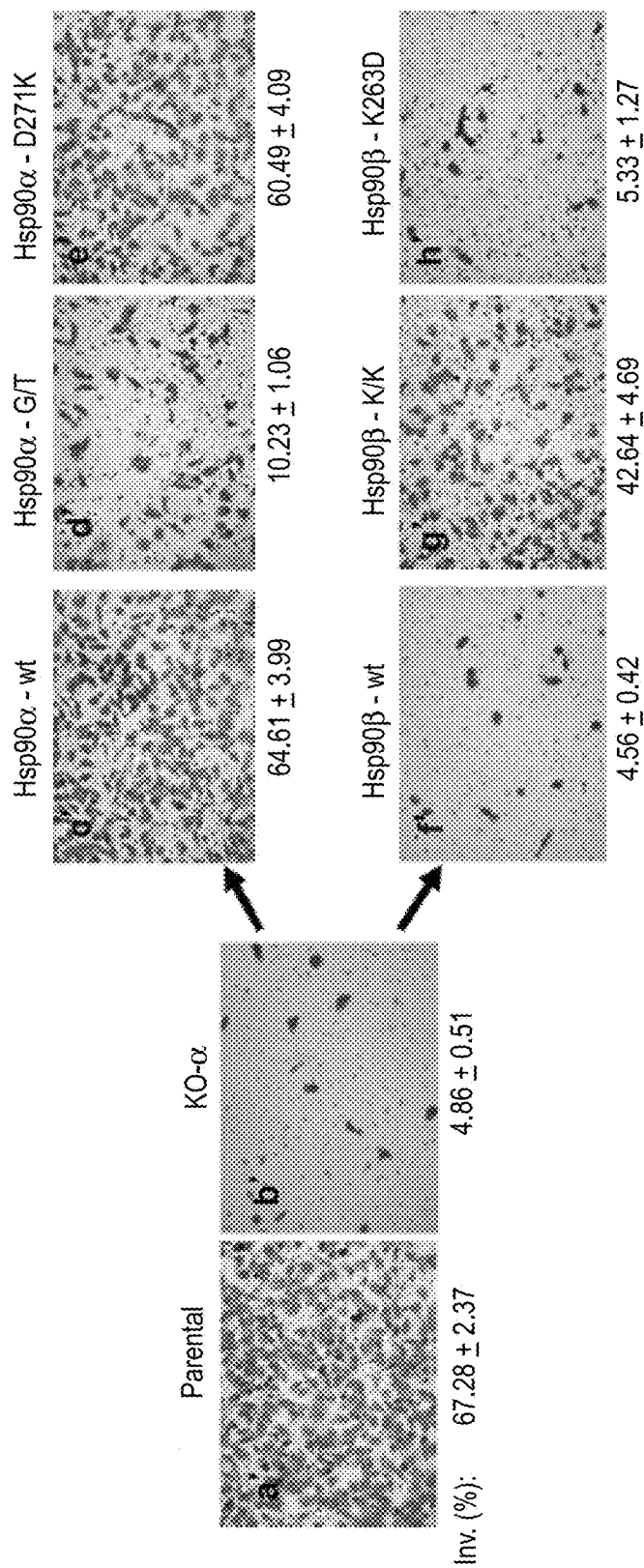
Figure 6E:
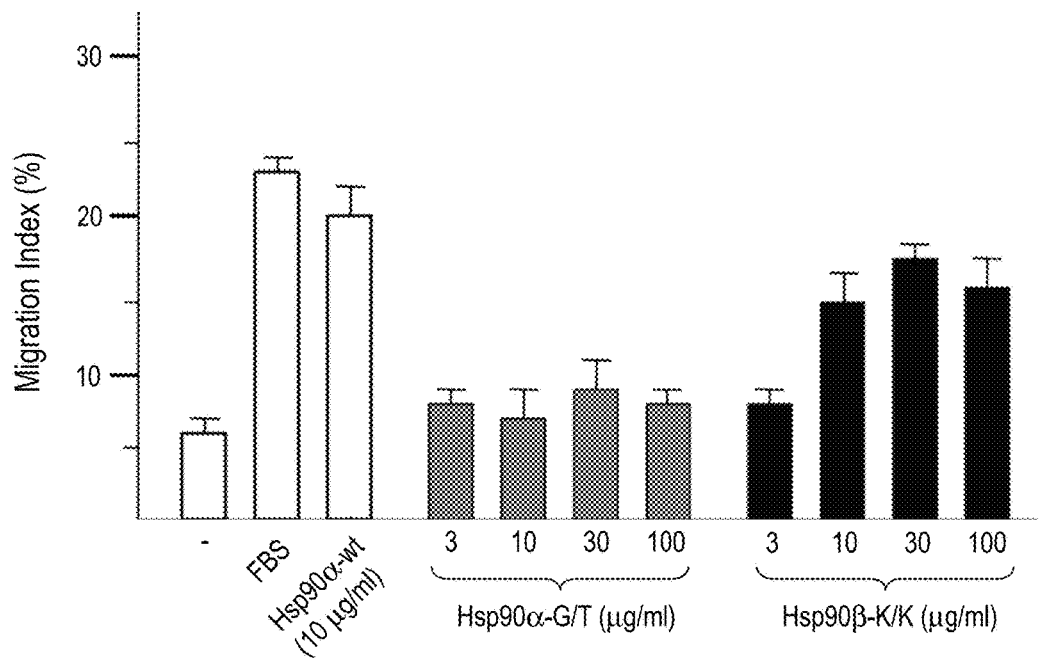
Figure 6F:
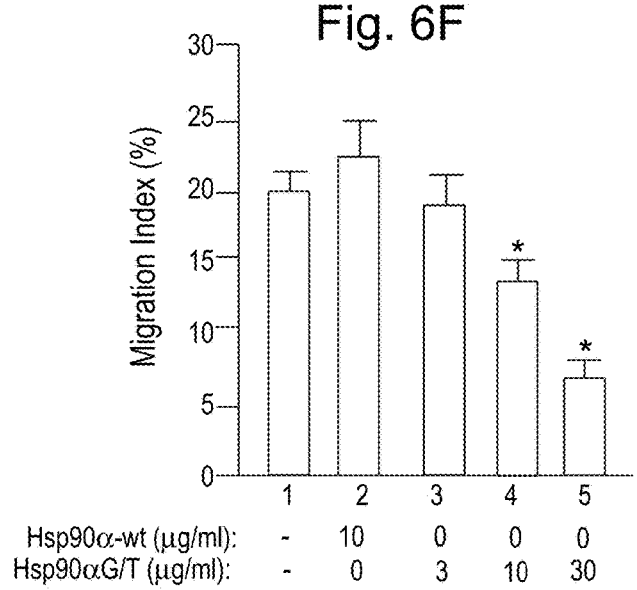

We used the Hsp90α-knockout MDA-MB-231 cell clones to test which of the six recombinant proteins rescues the motility and invasion defects of the cells under serum-free conditions. As shown in FIG. 6C, KO-α cells lost their motility in reference to parental control cells (panel b, vs. panel a). As expected, the addition of the wild type Hsp90α protein rescued the motility defect (panel c). In contrast, the Hsp90α-G/T mutant failed to rescue the motility defect (panel d vs. panels c). The non-specific Hsp90α-D271K mutant acted as the wild type Hsp90α, as expected (panel e vs. panel c). The wild type Hsp90β protein was unable to rescue the motility defect, as expected (panel f). The Hsp90β-K/K mutant protein acted just like the wild type Hsp90α to rescue the motility defect of the Hsp90α-knockout cells (panel g vs. panel f). In contrast, the non-specific Hsp90β-K263D mutant still acted as the wild type Hsp90β protein (panel h). The dose-dependent effects of Hsp90α-G/T and Hsp90β-K/K mutants on cell motility is shown in FIG. 6E. Moreover, since the Hsp90α-G/T mutant showed a dominant-negative effect on MDA-MB-231 cells' intrinsic motility (FIG. 6F), the lysine-270 and lysine-277 likely define the activity, but not the binding of Hsp90α to its target protein(s).

The loss-of-function effect of the Hsp90α-G/T mutant and the gain-of-function effect of the Hsp90β-K/K mutant were confirmed by invasion assays. As shown in FIG. 6D, the wild type Hsp90α effectively rescued the invasion defect of KO-α cells (panel c' vs. panel b'), while the rescue ability of the Hsp90α-G/T mutant was dramatically reduced (panel d'). The non-specific Hsp90α-D271K mutant still acted as wild type Hsp90α (panel e'). As expected, the wild type Hsp90β showed little rescue effect (panel f). The Hsp90β-K/K mutant, however, essentially turned into a wild type Hsp90α-like molecule with the ability to rescue KO-α cellular invasion (panel g' vs. panel b'). Taken together, we propose that, like the N-terminal ATPase domain that determines the intracellular chaperone function of Hsp90 family proteins, the lysine-270 and lysine-277 residues, which distinguish Hsp90α from Hsp90β, determine the extracellular function of tumor-secreted Hsp90α.

The new paradigm of targeting Hsp90 in cancer is: i) selectively inhibit the tumor cell-secreted Hsp90α (instead of its intracellular counterparts) and ii) specifically target the dual lysine area located at the linker region of the protein. Inhibitors, such as monoclonal antibodies described herein, that bear these two properties should achieve improved therapeutic efficacy with minimal toxicity.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for treating or preventing metastasis of HIF-1α-overexpressing cancer in a subject in need thereof comprising:
    administering a therapeutically effective amount of a composition comprising an inhibitor of Hsp90α to the subject,
    wherein the inhibitor of Hsp90α is a monoclonal antibody or a fragment thereof which binds TKPIWTRNP (SEQ ID NO: 1) epitope of Hsp90α or a monoclonal antibody or a fragment thereof which binds VKHFSVEGQ (SEQ ID NO: 2) epitope of Hsp90α, wherein the monoclonal antibody is selected from the group consisting of: a monoclonal antibody produced by hybridoma 1G6-D7, ATCC accession number PTA-125207 and a monoclonal antibody produced by hybridoma 5C4-D4, ATCC accession number PTA-125208,
    so as to treat or prevent metastasis of HIF-1α-overexpressing cancer in the subject.

2. The method of claim 1, wherein the cancer is breast cancer.

3. The method of claim 1, wherein the cancer is lung cancer.

4. The method of claim 1, wherein the inhibitor further targets amino acids Lys-270, Lys-277 or a combination thereof of Hsp90α.

5. The method of claim 1, wherein the inhibitor of Hsp90α is administered intravenously, intramuscularly, intraperitoneally, orally or via inhalation.

6. The method of claim 1, wherein the effective amount of the inhibitor of Hsp90α or fragments thereof is about 1-5 mg/kg/day, 5-10 mg/kg/day, 10-50 mg/kg/day, or 10-30 mg/kg/day.

7. The method of claim 1, further comprising administering additional cancer therapy to the subject, wherein the additional therapy is selected from chemotherapy, immunotherapy, radiation therapy or a combination thereof.

8. The method of claim 7, wherein the monoclonal antibody, or a fragment thereof, and the additional therapy are administered sequentially.

9. The method of claim 7, wherein the monoclonal antibody, or a fragment thereof, and the additional therapy are administered simultaneously.

10. The method of claim 1, wherein the therapeutically effective amount of the monoclonal antibody or a fragment thereof is 0.01 to 0.05 µg/kg/day, 0.05-0.1 µg/kg/day, 0.1 to 0.5 µg/kg/day, 0.5 to 5 µg/kg/day, 5 to 10 µg/kg/day, 10 to 20 µg/kg/day, 20 to 50 µg/kg/day, 50 to 100 µg/kg/day, 100 to 150 µg/kg/day, 150 to 200 µg/kg/day, 200 to 250 µg/kg/day, 250 to 300 µg/kg/day, 300 to 350 µg/kg/day, 350 to 400 µg/kg/day, 400 to 500 µg/kg/day, 500 to 600 µg/kg/day, 600 to 700 µg/kg/day, 700 to 800 µg/kg/day, 800 to 900 µg/kg/day, 900 to 1000 µg/kg/day or a combination thereof.

11. The method of claim 1, wherein the therapeutically effective amount of the monoclonal antibody or a fragment thereof is 0.01 to 0.05 mg/kg/day, 0.05-0.1 mg/kg/day, 0.1 to 0.5 mg/kg/day, 0.5 to 1 mg/kg/day, 1 to 5 mg/kg/day, 5 to 10 mg/kg/day, 10 to 15 mg/kg/day, 15 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day, 900 to 1000 mg/kg/day or a combination thereof.

12. The method of claim 1, wherein the monoclonal antibody or a fragment thereof is administered once a day (SID/QD), twice a day (BID), three times a day (TID), four times a day (QID), or more.

* * * * *

UNITED STATES PATENT AND TRADEMARK OFFICE
CERTIFICATE OF CORRECTION

| | |
|---|---|
| PATENT NO. | : 10,273,294 B2 |
| APPLICATION NO. | : 14/932908 |
| DATED | : April 30, 2019 |
| INVENTOR(S) | : Wei Li et al. |

It is certified that error appears in the above-identified patent and that said Letters Patent is hereby corrected as shown below:

In the Specification

Column 1, Lines 21-24, cancel the text beginning with "This invention was made with government support" and ending with "certain rights in the invention." and insert the following:
--This invention was made with government support under Grant Nos. GM066193, GM067100, AR033625, AR046538, and AR067100 awarded by the National Institutes of Health. The government has certain rights in the invention.--

Signed and Sealed this
Thirtieth Day of August, 2022

Katherine Kelly Vidal
*Director of the United States Patent and Trademark Office*